(12) United States Patent
Mansfield et al.

(10) Patent No.: US 9,120,815 B2
(45) Date of Patent: Sep. 1, 2015

(54) SOLID STATE FORMS OF MACROCYCLIC KINASE INHIBITORS

(75) Inventors: Robert K. Mansfield, Carlsbad, CA (US); Tracy Lawhon, Encinitas, CA (US); Brian Dymock, Buona Vista District (SG)

(73) Assignee: Tragara Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 13/577,208

(22) PCT Filed: Feb. 4, 2011

(86) PCT No.: PCT/US2011/023810
§ 371 (c)(1),
(2), (4) Date: Feb. 21, 2013

(87) PCT Pub. No.: WO2011/097525
PCT Pub. Date: Aug. 11, 2011

(65) Prior Publication Data
US 2013/0150378 A1 Jun. 13, 2013

Related U.S. Application Data

(60) Provisional application No. 61/301,771, filed on Feb. 5, 2010.

(51) Int. Cl.
| | |
|---|---|
| C07D 471/04 | (2006.01) |
| C07D 471/22 | (2006.01) |
| C07D 487/04 | (2006.01) |
| C07D 267/22 | (2006.01) |
| C07D 281/18 | (2006.01) |
| C07D 291/00 | (2006.01) |
| C07D 337/16 | (2006.01) |
| C07D 487/00 | (2006.01) |
| C07D 491/00 | (2006.01) |
| C07D 513/00 | (2006.01) |
| C07D 498/06 | (2006.01) |
| A61K 31/535 | (2006.01) |
| C07D 498/08 | (2006.01) |

(52) U.S. Cl.
CPC ........... *C07D 498/06* (2013.01); *A61K 31/535* (2013.01); *C07D 498/08* (2013.01)

(58) Field of Classification Search
None
See application file for complete search history.

(56) References Cited

U.S. PATENT DOCUMENTS

| | | | |
|---|---|---|---|
| 3,536,809 A | 10/1970 | Appelzweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,639,480 A | 6/1997 | Bodmer et al. | |
| 5,674,533 A | 10/1997 | Santus et al. | |
| 5,733,566 A | 3/1998 | Lewis | |
| 5,739,108 A | 4/1998 | Mitchell | |
| 5,891,474 A | 4/1999 | Busetti et al. | |
| 5,922,356 A | 7/1999 | Koseki et al. | |
| 5,972,891 A | 10/1999 | Kamei et al. | |
| 5,980,945 A | 11/1999 | Ruiz | |
| 5,993,855 A | 11/1999 | Yoshimoto et al. | |
| 6,045,830 A | 4/2000 | Igari et al. | |
| 6,087,324 A | 7/2000 | Igari et al. | |
| 6,113,943 A | 9/2000 | Okada et al. | |
| 6,197,350 B1 | 3/2001 | Yamagata et al. | |
| 6,248,363 B1 | 6/2001 | Patel et al. | |
| 6,264,970 B1 | 7/2001 | Hata et al. | |
| 6,267,981 B1 | 7/2001 | Okamoto et al. | |
| 6,376,461 B1 | 4/2002 | Igari et al. | |
| 6,419,961 B1 | 7/2002 | Igari et al. | |
| 6,589,548 B1 | 7/2003 | Oh et al. | |
| 6,613,358 B2 | 9/2003 | Randolph et al. | |
| 6,699,500 B2 | 3/2004 | Okada et al. | |
| 2009/0163428 A1 | 6/2009 | Chiu et al. | |
| 2009/0258886 A1* | 10/2009 | Blanchard et al. | ............ 514/257 |

FOREIGN PATENT DOCUMENTS

| | | |
|---|---|---|
| WO | WO 2007/058628 | 5/2007 |
| WO | WO 2007058628 A1 * | 5/2007 |

OTHER PUBLICATIONS

Morissette et al. in Drug Delivery Reviews, 56 (2004) 275-300.*
Baselga J., Science, 2006, 312, 1175-1178.
Berk BC et al, Circ. Res, 1997, 80, 607-616.
Cai D et al, Cancer Res, 2006, 66, 9270-9280.
Chemical Abstracts No. [937270-47-8]; also known as TGO2 or SB 1317.
Hannah AL, Curt-. Mol. Med., 2005, 5, 625-642.
Knockaert M et al, Trends Pharmacol. Sci., 2002, 23, 417-425.
Lim CP et al, Oncogene, 2006, 25, 5416-5425.
Parcells BW et al, Stem Cells, 2006, 24, 1174-1184.
Percy MJ of al, Hematol. Oncol., 2005, 23, 91-93.
PCT App No. PCT/US11/23810 International Search Report and Written Opinion mailed Apr. 4, 2011.
PCT App No. PCT/US11/23810 International Preliminary Report on Patentability mailed Aug. 7, 2012.
Rawlings JS et al, J. Cell Sci., 2004, 117, 1281-1283.
Samardzija M et al, FASEB J., 2006, 10, 1096.
Schafer Al, Blood, 2006, 107, 4214-4222.
Shapiro GI, J. Clin. Oncol., 2006, 24, 1770-1783.
Tickenbrock L et al, Expert Opin. Emerging Drugs, 2006, 11, 1-13.
EP11 740 460.8 European Extended Search Report mailed Nov. 7, 2013.

* cited by examiner

*Primary Examiner* — Dennis Heyer
*Assistant Examiner* — Daniel M Podgorski
(74) *Attorney, Agent, or Firm* — Wilson Sonsini Goodrich & Rosati

(57) ABSTRACT

Provided herein are salt forms of macrocyclic protein kinase inhibitors, pharmaceutical compositions containing the same, methods of making and using these compounds and compositions to treat proliferative disease mediated by kinase activity.

16 Claims, 38 Drawing Sheets

SOLID STATE FORMS OF MACROCYCLIC KINASE INHIBITORS

CROSS REFERENCE

This application is filed pursuant to 35 U.S.C. §371 as a United States National Phase Application of International Application No. PCT/US2011/23810, filed on Feb. 4, 2011, which claims the benefit of U.S. Provisional Application No. 61/301,771, filed Feb. 5, 2010 which is incorporated herein by reference in its entirety.

BACKGROUND OF THE INVENTION

The present disclosure relates to heterocyclic protein kinase inhibitors, solid state forms of the same, pharmaceutical compositions containing the same, methods of making and using these compounds and compositions to treat proliferative disease mediated by kinase activity.

SUMMARY OF THE INVENTION

One embodiment provides a citiric acid salt of 14-methyl-20-oxa-5,7,14,27-tetraazatetracyclo-[19.3.1.12,6.18,12]heptacosa-1(25),2,4,6,8,10,12(26),16,21,23-decaene.

One embodiment provides a fumaric acid salt of 14-methyl-20-oxa-5,7,14,27-tetraazatetracyclo-[19.3.1.12,6.18,12]heptacosa-1(25),2,4,6,8,10,12(26),16,21,23-decaene.

Another embodiment provides crystalline citrate pattern 1 of 14-methyl-20-oxa-5,7,14,27-tetraazatetracyclo-[19.3.1.12,6.18,12]heptacosa-1(25),2,4,6,8,10,12(26),16,21,23-decaene citrate.

Another embodiment provides crystalline citrate pattern 2 of 14-methyl-20-oxa-5,7,14,27-tetraazatetracyclo-[19.3.1.12,6.18,12]heptacosa-1(25),2,4,6,8,10,12(26),16,21,23-decaene citrate.

Another embodiment provides crystalline fumarate pattern 1 of 14-methyl-20-oxa-5,7,14,27-tetraazatetracyclo-[19.3.1.12,6.18,12]heptacosa-1(25),2,4,6,8,10,12(26),16,21,23-decaene fumarate.

Another embodiment provides crystalline fumarate pattern 2 of 14-methyl-20-oxa-5,7,14,27-tetraazatetracyclo-[19.3.1.12,6.18,12]heptacosa-1(25),2,4,6,8,10,12(26),16,21,23-decaene fumarate.

Another embodiment provides crystalline citrate pattern 1 of 14-methyl-20-oxa-5,7,14,27-tetraazatetracyclo-[19.3.1.12,6.18,12]heptacosa-1(25),2,4,6,8,10,12(26),16,21,23-decaene citrate having a melting point of 191° C. as determined by differential scanning calorimetry.

Another embodiment provides crystalline fumarate pattern 2 of 14-methyl-20-oxa-5,7,14,27-tetraazatetracyclo-[19.3.1.12,6.18,12]heptacosa-1(25),2,4,6,8,10,12(26),16,21,23-decaene fumarate having a melting point of 240° C. as determined by differential scanning calorimetry.

Another embodiment provides crystalline citrate pattern 1 of 14-methyl-20-oxa-5,7,14,27-tetraazatetracyclo-[19.3.1.12,6.18,12]heptacosa-1(25),2,4,6,8,10,12(26),16,21,23-decaene citrate characterized by a powder x-ray diffraction pattern having reflections at 2 theta=21.5°. In a further embodiment the composition is characterized by a powder x-ray diffraction pattern having reflections at 2 theta=21.5°, and 15.0°. In a further embodiment the composition is characterized by a powder x-ray diffraction pattern having reflections at 2 theta=21.5°, 19.8°, and 15.0°. In a further embodiment the composition is characterized by a powder x-ray diffraction pattern as provided in FIG. 13.

Another embodiment provides crystalline fumarate pattern 2 of 14-methyl-20-oxa-5,7,14,27-tetraazatetracyclo-[19.3.1.12,6.18,12]heptacosa-1(25),2,4,6,8,10,12(26),16,21,23-decaene fumarate characterized by a powder x-ray diffraction pattern having reflections at 2 theta=25.8°.

In a further embodiment the composition is characterized by a powder x-ray diffraction pattern having reflections at 2 theta=25.8°, and 23.8°. In a further embodiment the composition is characterized by a powder x-ray diffraction pattern having reflections at 2 theta=25.8°, 23.8°, and 23.0°. In a further embodiment the composition is characterized by a powder x-ray diffraction pattern as provided in FIG. 21.

Another embodiment provides crystalline citrate pattern 2 of 14-methyl-20-oxa-5,7,14,27-tetraazatetracyclo-[19.3.1.12,6.18,12]heptacosa-1(25),2,4,6,8,10,12(26),16,21,23-decaene citrate characterized by a powder x-ray diffraction pattern having reflections at 2 theta=20.6°. In a further embodiment the composition is characterized by a powder x-ray diffraction pattern having reflections at 2 theta=20.6°, and 24.5°.

Another embodiment provides crystalline fumarate pattern 1 of 14-methyl-20-oxa-5,7,14,27-tetraazatetracyclo-[19.3.1.12,6.18,12]heptacosa-1(25),2,4,6,8,10,12(26),16,21,23-decaene fumarate characterized by a powder x-ray diffraction pattern having reflections at 2 theta=14.9°. In a further embodiment the composition is characterized by a powder x-ray diffraction pattern having reflections at 2 theta=7.1°, and 14.9°.

One embodiment provides a benzene sulfonic acid salt of 14-methyl-20-oxa-5,7,14,27-tetraazatetracyclo-[19.3.1.12,6.18,12]heptacosa-1(25),2,4,6,8,10,12(26),16,21,23-decaene. Another embodiment provides crystalline besylate pattern 1 of 14-methyl-20-oxa-5,7,14,27-tetraazatetracyclo-[19.3.1.12,6.18,12]heptacosa-1(25),2,4,6,8,10,12(26),16,21,23-decaene besylate.

One embodiment provides a pharmaceutical composition comprising a therapeutically effective amount of crystalline citrate pattern 1 of 14-methyl-20-oxa-5,7,14,27-tetraazatetracyclo-[19.3.1.12,6.18,12]heptacosa-1(25),2,4,6,8,10,12(26),16,21,23-decaene citrate. One embodiment provides a pharmaceutical composition comprising a therapeutically effective amount of crystalline citrate pattern 2 of 14-methyl-20-oxa-5,7,14,27-tetraazatetracyclo-[19.3.1.12,6.18,12]heptacosa-1(25),2,4,6,8,10,12(26),16,21,23-decaene citrate. Another embodiment provides the pharmaceutical composition substantially free of any other solid state form of 14-methyl-20-oxa-5,7,14,27-tetraazatetracyclo-[19.3.1.12,6.18,12]heptacosa-1(25),2,4,6,8,10,12(26),16,21,23-decaene citrate.

One embodiment provides a pharmaceutical composition comprising a therapeutically effective amount of crystalline fumarate pattern 1 of 14-methyl-20-oxa-5,7,14,27-tetraazatetracyclo-[19.3.1.12,6.18,12]heptacosa-1(25),2,4,6,8,10,12(26),16,21,23-decaene fumarate. One embodiment provides a pharmaceutical composition comprising a therapeutically effective amount of crystalline fumarate pattern 2 of 14-methyl-20-oxa-5,7,14,27-tetraazatetracyclo-[19.3.1.12,6.18,12]heptacosa-1(25),2,4,6,8,10,12(26),16,21,23-decaene fumarate. Another embodiment provides the pharmaceutical composition substantially free of any other solid state form of 14-methyl-20-oxa-5,7,14,27-tetraazatetracyclo-[19.3.1.12,6.18,12]heptacosa-1(25),2,4,6,8,10,12(26),16,21,23-decaene fumarate.

One embodiment provides a pharmaceutical composition comprising a therapeutically effective amount of crystalline besylate pattern 1 of 14-methyl-20-oxa-5,7,14,27-tetraazatetracyclo-[19.3.1.12,6.18,12]heptacosa-1(25),2,4,6,8,10,12

(26),16,21,23-decaene besylate. Another embodiment provides the pharmaceutical composition substantially free of any other solid state form of 14-methyl-20-oxa-5,7,14,27-tetraazatetracyclo-[19.3.1.1²,⁶.1⁸,¹²]heptacosa-1(25),2,4,6,8,10,12(26),16,21,23-decaene besylate.

One embodiment provides a method of treating proliferative disease comprising administering a therapeutically effective amount of the pharmaceutical composition comprising a therapeutically effective amount of crystalline citrate pattern 1 of 14-methyl-20-oxa-5,7,14,27-tetraazatetracyclo-[19.3.1.1²,⁶.1⁸,¹²]heptacosa-1(25),2,4,6,8,10,12(26),16,21,23-decaene citrate.

One embodiment provides a method of treating proliferative disease comprising administering a therapeutically effective amount of the pharmaceutical composition comprising a therapeutically effective amount of crystalline citrate pattern 2 of 14-methyl-20-oxa-5,7,14,27-tetraazatetracyclo-[19.3.1.1²,⁶.1⁸,¹²]heptacosa-1(25),2,4,6,8,10,12(26),16,21,23-decaene citrate.

One embodiment provides a method of treating proliferative disease comprising administering a therapeutically effective amount of the pharmaceutical composition comprising a therapeutically effective amount of crystalline fumarate pattern 1 of 14-methyl-20-oxa-5,7,14,27-tetraazatetracyclo-[19.3.1.1²,⁶.1⁸,¹²]heptacosa-1(25),2,4,6,8,10,12(26),16,21,23-decaene fumarate.

One embodiment provides a method of treating proliferative disease comprising administering a therapeutically effective amount of the pharmaceutical composition comprising a therapeutically effective amount of crystalline fumarate pattern 2 of 14-methyl-20-oxa-5,7,14,27-tetraazatetracyclo-[19.3.1.1²,⁶.1⁸,¹²]heptacosa-1(25),2,4,6,8,10,12(26),16,21,23-decaene fumarate.

One embodiment provides a method of treating proliferative disease comprising administering a therapeutically effective amount of the pharmaceutical composition comprising a therapeutically effective amount of crystalline besylate pattern 1 of 14-methyl-20-oxa-5,7,14,27-tetraazatetracyclo-[19.3.1.1²,⁶.1⁸,¹²]heptacosa-1(25),2,4,6,8,10,12(26),16,21,23-decaene besylate.

Another embodiment provides the method wherein the proliferative disease is cancer. Another embodiment provides the method wherein the cancer is a hematological or myeloproliferative cancer. Another embodiment provides the method wherein the cancer is a solid tumor. Another embodiment provides the method wherein the cancer is characterized by increased Flt3, CDK or JAK signaling.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The features of the invention are set forth with particularity in the appended claims. A better understanding of the features of the present invention will be obtained by reference to the following detailed description that sets forth illustrative embodiments, in which the principles of the invention are utilized, and the accompanying drawings of which:

FIGS. 7 and 8 show the GVS curves of Compound I at 25° C., wherein
FIG. 7 illustrates two cycles of sorption and desorption and FIG. 8 illustrates the change in mass as a function of time and varying relative humidity wherein at time equal zero the upper trace represents target relative humidity and the lower trace represents change in mass (dm-dry);
FIGS. 16 and 17 shows the GVS at 25° C. curves of the citrate pattern 1 polymorph of Compound I wherein
FIG. 16 illustrates two cycles of sorption and desorption wherein at 40% target RH the upper trace represents cycle 1 sorption, the second trace represents cycle 1 desorption, the middle trace represents cycle 2 desorption, the fourth trace represents cycle 2 sorption and the bottom trace represents cycle 3 sorption
and FIG. 17 illustrates the change in mass as a function of time and varying relative humidity wherein at time equal 1000 the upper trace represents target relative humidity and the lower trace represents change in mass (dm-dry)

24 illustrates two cycles of sorption and desorption wherein at 40% target RH the upper trace represents cycle 1 sorption, the second trace represents cycle 1 desorption, the middle trace represents cycle 2 sorption, the fourth trace represents cycle 2 desorption and the bottom trace represents cycle 3 sorption and FIG. 25 illustrates the change in mass as a function of time and varying relative humidity wherein at time equal 700 the upper trace represents target relative humidity and the lower trace represents change in mass (dm-dry);

DETAILED DESCRIPTION OF THE INVENTION

Figure 1:
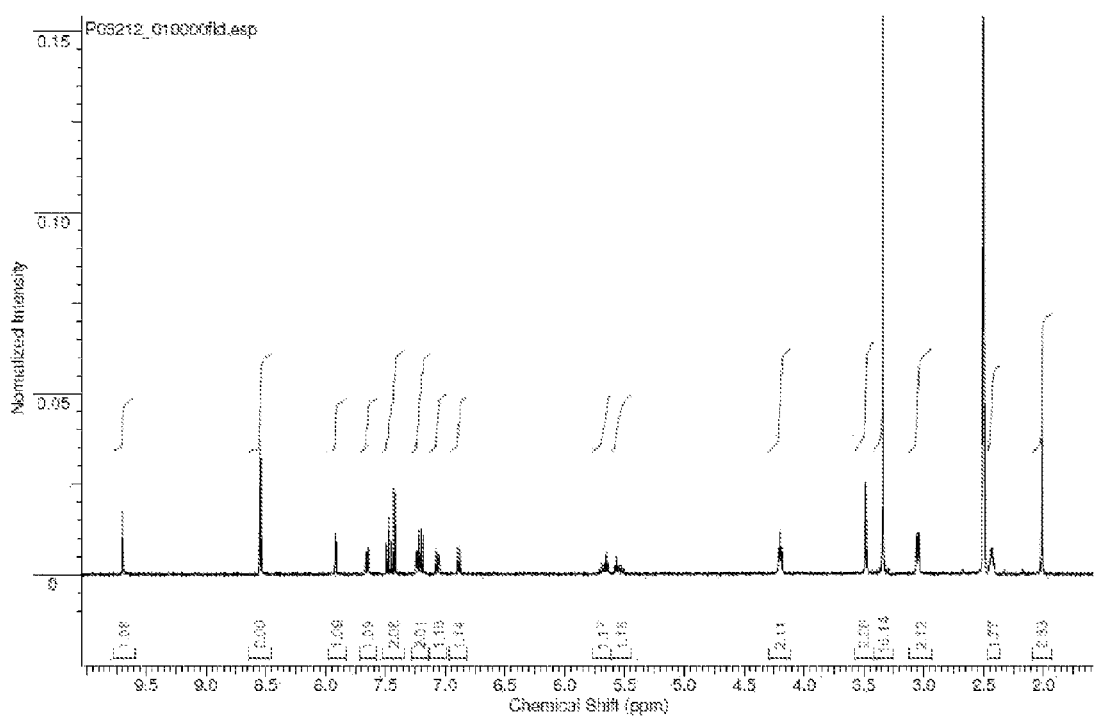
FIG. 1 shows the $^1$H NMR spectrum of Compound I.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

One of the major advances in cancer research has been the clinical validation of molecularly targeted drugs that inhibit the activity of protein kinases. Small-molecule kinase inhibitors that are now approved for oncology indications include imatinib, gefitinib, erlotinib, sorafenib, sunitinib and dasatinib (Baselga J., Science, 2006, 312, 1175-1178). A number of kinases such as JAK2, FLT3 and CDK2 are promising kinase targets for pharmacological intervention in solid tumours, hematological malignancies, myeloproliferative disorders and non-malignant proliferative disorders like keloids. The Janus kinases (JAK) are a family of cytoplasmic tyrosine kinases consisting of JAK1, JAK2, JAK3 and Tyk2. They play a pivotal role in the signaling pathways of numerous cytokines, hormones and growth factors (Rawlings J S et al, J. Cell Sci., 2004, 117, 1281-1283). Their intracellular substrates include the family of proteins called Signal Transducer and Activator of Transcription (STAT). The JAK-STAT pathways, through the proper actions of the ligands, regulate important physiological processes such as immune response to viruses, erythropoiesis, lactation, lipid homeostasis, etc. However, dysfunctional signaling caused by a myriad of factors result in pathophysiological conditions such as allergies, asthma, rheumatoid arthritis, severe combined immune deficiency, hematological malignancies, etc. In particular, mutations in JAK2 have been associated with myeloproliferative disorders (including polycythemia vera, essential thrombocythemia and idiopathic myelofibrosis) and a wide range of leukemias and lymphomas (Percy M J of al, Hematol. Oncol., 2005, 23, 91-93). Importantly, the myeloproliferative disorders belong to an area of unmet medical need where some treatment modalities have not been updated over the past few decades (Schafer Al, Blood, 2006, 107, 4214-4222).

The myeloproliferative disorders (MPDs) belong to a group of hematological malignancies arising from clonal expansion of mutated progenitor stem cells in the bone marrow. The association of one MPD, chronic myeloid leukemia, with the Philadelphia chromosome has been well documented. The Philadelphia negative MPDs include Essential Thrombocythemia (ET), Polycythemia Vera (PV) and Chronic Idiopathic Myelofibrosis (MF). No effective treatment is currently available. The recent discovery that a single acquired somatic mutation in JAK2 appears responsible for many of the features of these MPDs promises to impact the diagnosis and treatment of patients with these disorders and to spur additional research into the origins of dysregulated cell growth and function. Until recently, most MPDs have been considered to be rare or orphan diseases but studies underway suggest a much higher prevalence.

Essential Thrombocythemia is a chronic MPD characterized by an increased number of circulating platelets, profound marrow megakaryocyte hyperplasia, splenomegaly and a clinical course punctuated by hemorrhagic or thrombotic episodes or both. Current treatment options include low dose aspirin, or platelet lowering agents such as anagrelide, interferon or hydroxyurea. These treatments have severe side effects that compromise the quality of life of patients.

Polycythemia Vera is a chronic progressive MPD characterized by an elevated hematocrit, an increase in the red cell mass, and usually by an elevated leukocyte count, an elevated platelet count and an enlarged spleen. The most common cause of morbidity and mortality is the predisposition of PV patients to develop life threatening arterial and venous thromboses. Treatment options include: phlebotomy with low dose aspirin or myelosuppressive therapy options such as hydroxyurea, interferon or anagrelide. Again, these treatments are not ideal due to severe side effects.

Chronic Idiopathic Myelofibrosis (MF) is a chronic malignant hematological disorder characterized by an enlarged spleen, varying degrees of anemia and low platelet counts, red cells in the peripheral blood that resemble tear drops, the appearance of small numbers of immature nucleated red cells and white cells in the blood, varying degrees of fibrosis of the marrow cavity (myelofibrosis) and the presence of marrow cells outside the marrow cavity (extramedullar hematopoiesis or myeloid metaplasia). Current treatment is directed at alleviation of constitutional symptoms, anemia and symptomatic splenomegaly. Treatment options include hydroxyurea, interferon, thalidomide with prednisone, and allogeneic stem cell transplant. MF has the worst prognosis among the Philadelphia negative MPD and represents an area of greatest unmet medical need.

In addition, due to its role in the angiotensin II signaling pathway, JAK2 is also implicated in the etiology of cardiovascular diseases like congestive heart failure and pulmonary hypertension (Berk B C et al, Circ. Res, 1997, 80, 607-616). Furthermore, a putative role for JAK2 has been demonstrated in keloid pathogenesis and may constitute a new approach for keloid management (Lim C P et al, Oncogene, 2006, 25, 5416-5425). Yet another potential application for JAK2 inhibitors lies in the treatment of retinal diseases as JAK2 inhibition was found to offer protective effects on photoreceptors in a mouse model of retinal degeneration (Samardzija M et al, FASEB J., 2006, 10, 1096).

A family of Class III receptor tyrosine kinases (RTK), including c-Fms, c-Kit, fms-like receptor tyrosine kinase 3 (FLT3), and platelet-derived growth factor receptors (PDGFRfct and (β), play an important role in the maintenance, growth and development of hematopoietic and non-hematopoietic cells. Overexpression and activating mutations of these RTKs are known to be involved in the pathophysiology of diverse human cancers from both solid and hematological origins (Hannah A L, Curr. Mol. Med., 2005, 5, 625-642). FLT3 mutations were first reported as internal tandem duplication (FLT3/ITD) of the juxtamembrane domain-coding sequence; subsequently, point mutations, deletions and insertions surrounding the D835 coding sequence have been found (Parcells B W et al, Stem Cells, 2006, 24, 1174-1184). FLT3 mutations are the most frequent genetic alterations reported in acute myeloid leukemia (AML) and are involved in the signaling pathway of autonomous proliferation and differentiation block in leukemia cells (Tickenbrock L et al, Expert Opin. Emerging Drugs, 2006, 11, 1-13). Several clinical studies have confirmed that FLT3/ITD is strongly associated with a poor prognosis. Because high-dose chemotherapy and stem cell transplantation cannot overcome the adverse effects of FLT3 mutations, the development of FLT3 kinase inhibitors could produce a more efficacious therapeutic strategy for leukemia therapy.

Cyclin-dependent kinases (CDKs) are serine-threonine kinases that play important roles in cell cycle control (CDK1, 2, 4 and 6), transcription initiation (CDK7 and 9), and neuronal function (CDK5) (Knockaert M et al, Trends Pharmacol. Sci., 2002, 23, 417-425). Aberrations in the cell cycle CDKs and their cyclin partners have been observed in various tumour types, including those of the breast, colon, liver and brain (Shapiro G I, J. Clin. Oncol., 2006, 24, 1770-1783). It is believed that the pharmacological inhibition of CDK1, 2, 4, 6 and/or 9 may provide a new therapeutic option for diverse cancer patients. In particular, the simultaneous inhibition of CDK1, 2 and 9 has recently been shown to result in enhanced apoptotic killing of lung cancer (H1299) and osteosarcoma cells (U2OS), compared with inhibition of single CDK alone (Cai D et al, Cancer Res, 2006, 66, 9270-9280).

Accordingly, compounds that are kinase inhibitors have the potential to provide further biologically active compounds that would be expected to have useful, improved pharmaceutical properties in the treatment of kinase related conditions or disorders such as cancer and other proliferative disorders.

Provided herein is 14-methyl-20-oxa-5,7,14,27-tetraazatetracyclo-[19.3.1.12,6.18,12]heptacosa-1(25),2,4,6,8,10,12 (26),16,21,23-decaene (Chemical Abstracts Number [937270-47-8]; also known as TG02 or SB1317) and referred to herein as Compound I.

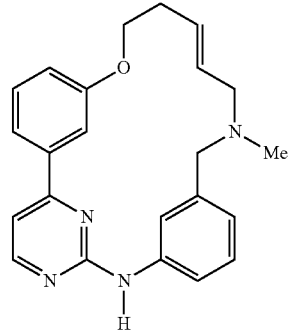

Compound I 14-methyl-20-Oxa-5,7,14,27-tetraazatetracyclo[19.3.1.12,6.18,12]heptacosa-1(25),2,4,6,8,10,12(26),16,21,23-decaene Compound I is a potent in vitro inhibitor of CDK2, FLT3, JAK2 and JAK V617F with an $IC_{50}$ less than 1 µM. In cell-based assays, Compound I exhibits a $GI_{50}$ less than 1 µM in HL60, Colo205, HEL92.1.7, MV4-11 and DU145 cell lines. The synthesis and biological activity of Compound I was reported in WO 2007/058628 which is incorporated by reference in its entirety. It has been found, however, that the physiochemical properties of Compound I are poor, for example the solubility in water has been determined to be less than 0.001 mg/mL, thus limiting the utility of Compound I as a therapeutic agent.

One embodiment provides a citiric acid salt of 14-methyl-20-oxa-5,7,14,27-tetraazatetracyclo-[19.3.1.12,6.18,12] heptacosa-1(25),2,4,6,8,10,12(26),16,21,23-decaene.

One embodiment provides a fumaric acid salt of 14-methyl-20-oxa-5,7,14,27-tetraazatetracyclo-[19.3.1.12,6.18, 12]heptacosa-1(25),2,4,6,8,10,12(26),16,21,23-decaene.

Another embodiment provides crystalline citrate pattern 1 of 14-methyl-20-oxa-5,7,14,27-tetraazatetracyclo-[19.3.1.12,6.18,12]heptacosa-1(25),2,4,6,8,10,12(26),16, 21,23-decaene citrate.

Another embodiment provides crystalline citrate pattern 2 of 14-methyl-20-oxa-5,7,14,27-tetraazatetracyclo-[19.3.1.12,6.18,12]heptacosa-1(25),2,4,6,8,10,12(26),16, 21,23-decaene citrate.

Another embodiment provides crystalline fumarate pattern 1 of 14-methyl-20-oxa-5,7,14,27-tetraazatetracyclo-[19.3.1.12,6.18,12]heptacosa-1(25),2,4,6,8,10,12(26),16, 21,23-decaene fumarate.

Another embodiment provides crystalline fumarate pattern 2 of 14-methyl-20-oxa-5,7,14,27-tetraazatetracyclo-[19.3.1.12,6.18,12]heptacosa-1(25),2,4,6,8,10,12(26),16,21,23-decaene fumarate.

Another embodiment provides crystalline citrate pattern 1 of 14-methyl-20-oxa-5,7,14,27-tetraazatetracyclo-[19.3.1.12,6.18,12]heptacosa-1(25),2,4,6,8,10,12(26),16,21,23-decaene citrate having a melting point of 191° C. as determined by differential scanning calorimetry.

Another embodiment provides crystalline fumarate pattern 2 of 14-methyl-20-oxa-5,7,14,27-tetraazatetracyclo-[19.3.1.12,6.18,12]heptacosa-1(25),2,4,6,8,10,12(26),16,21,23-decaene fumarate having a melting point of 240° C. as determined by differential scanning calorimetry.

Figure 13:
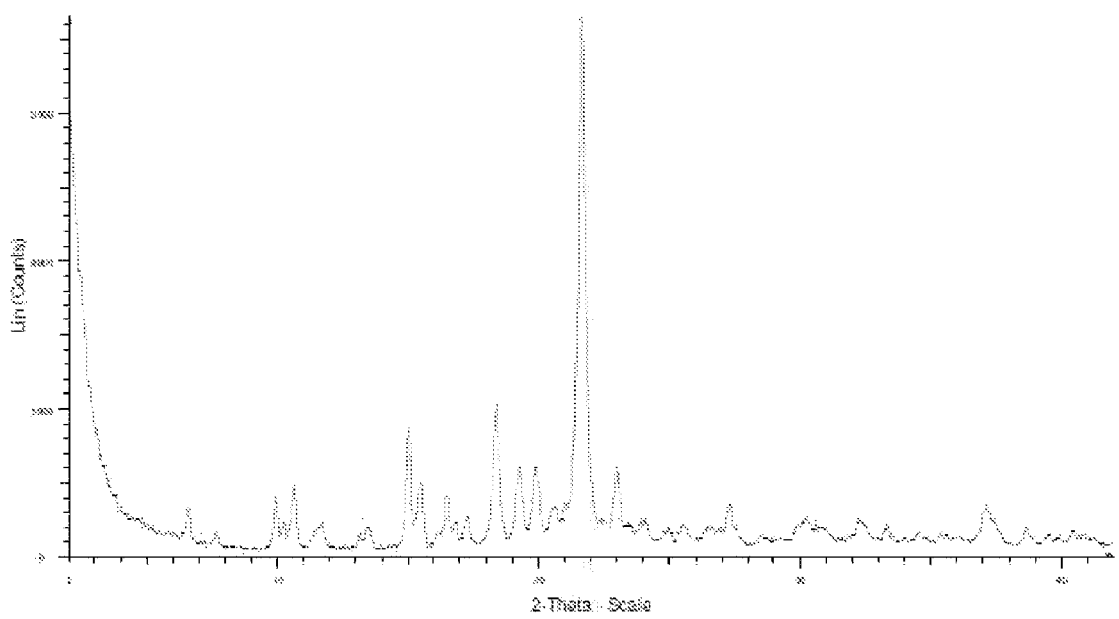
FIG. 13 shows the high resolution XRPD of the citrate pattern 1 polymorph of Compound I.

Another embodiment provides crystalline citrate pattern 1 of 14-methyl-20-oxa-5,7,14,27-tetraazatetracyclo-[19.3.1.12,6.18,12]heptacosa-1(25),2,4,6,8,10,12(26),16,21,23-decaene citrate characterized by a powder x-ray diffraction pattern having reflections at 2 theta=21.5°. In a further embodiment the composition is characterized by a powder x-ray diffraction pattern having reflections at 2 theta=21.5°, and 15.0°. In a further embodiment the composition is characterized by a powder x-ray diffraction pattern having reflections at 2 theta=21.5°, 19.8°, and 15.0°. In a further embodiment the composition is characterized by a powder x-ray diffraction pattern as provided in FIG. 13.

Another embodiment provides crystalline fumarate pattern 2 of 14-methyl-20-oxa-5,7,14,27-tetraazatetracyclo-[19.3.1.12,6.18,12]heptacosa-1(25),2,4,6,8,10,12(26),16,21,23-decaene fumarate characterized by a powder x-ray diffraction pattern having reflections at 2 theta=25.8°. In a further embodiment the composition is characterized by a powder x-ray diffraction pattern having reflections at 2 theta=25.8°, and 23.8°. In a further embodiment the composition is characterized by a powder x-ray diffraction pattern having reflections at 2 theta=25.8°, 23.8°, and 23.0°. In a further embodiment the composition is characterized by a powder x-ray diffraction pattern as provided in FIG. 21.

Another embodiment provides crystalline citrate pattern 2 of 14-methyl-20-oxa-5,7,14,27-tetraazatetracyclo-[19.3.1.12,6.18,12]heptacosa-1(25),2,4,6,8,10,12(26),16,21,23-decaene citrate characterized by a powder x-ray diffraction pattern having reflections at 2 theta=20.6°. In a further embodiment the composition is characterized by a powder x-ray diffraction pattern having reflections at 2 theta=20.6°, and 24.5°.

Another embodiment provides crystalline fumarate pattern 1 of 14-methyl-20-oxa-5,7,14,27-tetraazatetracyclo-[19.3.1.12,6.18,12]heptacosa-1(25),2,4,6,8,10,12(26),16,21,23-decaene fumarate characterized by a powder x-ray diffraction pattern having reflections at 2 theta=14.9°. In a further embodiment the composition is characterized by a powder x-ray diffraction pattern having reflections at 2 theta=7.1°, and 14.9°.

One embodiment provides a benzene sulfonic acid salt of 14-methyl-20-oxa-5,7,14,27-tetraazatetracyclo-[19.3.1.12,6.18,12]heptacosa-1(25),2,4,6,8,10,12(26),16,21,23-decaene. Another embodiment provides crystalline besylate pattern 1 of 14-methyl-20-oxa-5,7,14,27-tetraazatetracyclo-[19.3.1.12,6.18,12]heptacosa-1(25),2,4,6,8,10,12(26),16,21,23-decaene besylate.

One embodiment provides a pharmaceutical composition comprising a therapeutically effective amount of crystalline citrate pattern 1 of 14-methyl-20-oxa-5,7,14,27-tetraazatetracyclo-[19.3.1.12,6.18,12]heptacosa-1(25),2,4,6,8,10,12(26),16,21,23-decaene citrate. One embodiment provides a pharmaceutical composition comprising a therapeutically effective amount of crystalline citrate pattern 2 of 14-methyl-20-oxa-5,7,14,27-tetraazatetracyclo-[19.3.1.12,6.18,12]heptacosa-1(25),2,4,6,8,10,12(26),16,21,23-decaene citrate. Another embodiment provides the pharmaceutical composition substantially free of any other solid state form of 14-methyl-20-oxa-5,7,14,27-tetraazatetracyclo-[19.3.1.12,6.18,12]heptacosa-1(25),2,4,6,8,10,12(26),16,21,23-decaene citrate.

One embodiment provides a pharmaceutical composition comprising a therapeutically effective amount of crystalline fumarate pattern 1 of 14-methyl-20-oxa-5,7,14,27-tetraazatetracyclo-[19.3.1.12,6.18,12]heptacosa-1(25),2,4,6,8,10,12(26),16,21,23-decaene fumarate. One embodiment provides a pharmaceutical composition comprising a therapeutically effective amount of crystalline fumarate pattern 2 of 14-methyl-20-oxa-5,7,14,27-tetraazatetracyclo-[19.3.1.12,6.18,12]heptacosa-1(25),2,4,6,8,10,12(26),16,21,23-decaene fumarate. Another embodiment provides the pharmaceutical composition substantially free of any other solid state form of 14-methyl-20-oxa-5,7,14,27-tetraazatetracyclo-[19.3.1.12,6.18,12]heptacosa-1(25),2,4,6,8,10,12(26),16,21,23-decaene fumarate.

One embodiment provides a pharmaceutical composition comprising a therapeutically effective amount of crystalline besylate pattern 1 of 14-methyl-20-oxa-5,7,14,27-tetraazatetracyclo-[19.3.1.12,6.18,12]heptacosa-1(25),2,4,6,8,10,12(26),16,21,23-decaene besylate. Another embodiment provides the pharmaceutical composition substantially free of any other solid state form of 14-methyl-20-oxa-5,7,14,27-tetraazatetracyclo-[19.3.1.12,6.18,12]heptacosa-1(25),2,4,6,8,10,12(26),16,21,23-decaene besylate.

One embodiment provides a method of treating proliferative disease comprising administering a therapeutically effective amount of the pharmaceutical composition comprising a therapeutically effective amount of crystalline citrate pattern 1 of 14-methyl-20-oxa-5,7,14,27-tetraazatetracyclo-[19.3.1.12,6.18,12]heptacosa-1(25),2,4,6,8,10,12(26),16,21,23-decaene citrate.

One embodiment provides a method of treating proliferative disease comprising administering a therapeutically effective amount of the pharmaceutical composition comprising a therapeutically effective amount of crystalline citrate pattern 2 of 14-methyl-20-oxa-5,7,14,27-tetraazatetracyclo-[19.3.1.12,6.18,12]heptacosa-1(25),2,4,6,8,10,12(26),16,21,23-decaene citrate.

One embodiment provides a method of treating proliferative disease comprising administering a therapeutically effective amount of the pharmaceutical composition comprising a therapeutically effective amount of crystalline fumarate pattern 1 of 14-methyl-20-oxa-5,7,14,27-tetraazatetracyclo-[19.3.1.12,6.18,12]heptacosa-1(25),2,4,6,8,10,12(26),16,21,23-decaene fumarate.

One embodiment provides a method of treating proliferative disease comprising administering a therapeutically effective amount of the pharmaceutical composition comprising a therapeutically effective amount of crystalline fumarate pattern 2 of 14-methyl-20-oxa-5,7,14,27-tetraazatetracyclo-[19.3.1.12,6.18,12]heptacosa-1(25),2,4,6,8,10,12(26),16,21,23-decaene fumarate.

One embodiment provides a method of treating proliferative disease comprising administering a therapeutically effective amount of the pharmaceutical composition comprising a therapeutically effective amount of crystalline besylate pattern 1 of 14-methyl-20-oxa-5,7,14,27-tetraazatetracyclo-[19.3.1.12,6.18,12]heptacosa-1(25),2,4,6,8,10,12(26),16,21,23-decaene besylate.

Another embodiment provides the method wherein the proliferative disease is cancer. Another embodiment provides the method wherein the cancer is a hematological or myeloproliferative cancer. Another embodiment provides the method wherein the cancer is a solid tumor. Another embodiment provides the method wherein the cancer is characterized by increased Flt3, CDK or JAK signaling.

Pharmaceutical Compositions

Provided herein are pharmaceutical compositions comprising citrate, fumarate or besylate addition salts of Compound I as the active ingredient and one or more pharmaceutically acceptable excipients or carriers. In various embodiments, the pharmaceutical composition comprises a pharmaceutically acceptable vehicle, carrier, diluent, or excipient, or a mixture thereof.

Provided herein are pharmaceutical compositions comprising a therapeutically effective amount of crystalline citrate pattern 1 of 14-methyl-20-oxa-5,7,14,27-tetraazatetracyclo-[19.3.1.12,6.18,12]heptacosa-1(25),2,4,6,8,10,12(26), 16,21,23-decaene citrate as the active ingredient and one or more pharmaceutically acceptable excipients or carriers. In various embodiments, the pharmaceutical composition comprises a pharmaceutically acceptable vehicle, carrier, diluent, or excipient, or a mixture thereof.

Provided herein are pharmaceutical compositions comprising a therapeutically effective amount of crystalline citrate pattern 2 of 14-methyl-20-oxa-5,7,14,27-tetraazatetracyclo-[19.3.1.12,6.18,12]heptacosa-1(25),2,4,6,8,10,12(26), 16,21,23-decaene citrate as the active ingredient and one or more pharmaceutically acceptable excipients or carriers. In various embodiments, the pharmaceutical composition comprises a pharmaceutically acceptable vehicle, carrier, diluent, or excipient, or a mixture thereof.

Provided herein are pharmaceutical compositions comprising a therapeutically effective amount of crystalline fumarate pattern 1 of 14-methyl-20-oxa-5,7,14,27-tetraazatetracyclo-[19.3.1.12,6.18,12]heptacosa-1(25),2,4,6,8,10,12 (26),16,21,23-decaene fumarate as the active ingredient and one or more pharmaceutically acceptable excipients or carriers. In various embodiments, the pharmaceutical composition comprises a pharmaceutically acceptable vehicle, carrier, diluent, or excipient, or a mixture thereof.

Provided herein are pharmaceutical compositions comprising a therapeutically effective amount of crystalline fumarate pattern 2 of 14-methyl-20-oxa-5,7,14,27-tetraazatetracyclo-[19.3.1.12,6.18,12]heptacosa-1(25),2,4,6,8,10,12 (26),16,21,23-decaene fumarate as the active ingredient and one or more pharmaceutically acceptable excipients or carriers. In various embodiments, the pharmaceutical composition comprises a pharmaceutically acceptable vehicle, carrier, diluent, or excipient, or a mixture thereof.

Provided herein are pharmaceutical compositions comprising a therapeutically effective amount of crystalline besylate pattern 1 of 14-methyl-20-oxa-5,7,14,27-tetraazatetracyclo-[19.3.1.12,6.18,12]heptacosa-1(25),2,4,6,8,10,12(26), 16,21,23-decaene besylate as the active ingredient and one or more pharmaceutically acceptable excipients or carriers. In various embodiments, the pharmaceutical composition comprises a pharmaceutically acceptable vehicle, carrier, diluent, or excipient, or a mixture thereof.

Provided herein are pharmaceutical compositions in film-coated dosage forms, which comprise a combination of an active ingredient, and one or more tabletting excipients to form a tablet core using conventional tabletting processes and subsequently coating the core. The tablet cores can be produced using conventional granulation methods, for example wet or dry granulation, with optional comminution of the granules and with subsequent compression and coating.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient sufficient to produce the desired therapeutic effect, in association with the required pharmaceutical carriers or excipients. Examples of unit-dosage forms include ampules, syringes, and individually packaged tablets and -capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials or bottles of tablets or capsules.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In the case wherein the patient's condition does not improve, upon the doctor's discretion the administration of the combinations may be administered chronically, that is, for an extended period of time, including throughout the duration of the patient's life in order to ameliorate or otherwise control or limit the symptoms of the patient's disease or condition. In the case wherein the patient's status does improve, upon the doctor's discretion the administration of the combinations may be given continuously or temporarily suspended for a certain length of time (i.e., a "drug holiday"). In some embodiments, once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

Treatment dosages generally may be titrated to optimize safety and efficacy. Typically, dosage-effect relationships from in vitro studies initially can provide useful guidance on the proper doses for patient administration. Studies in animal models also generally may be used for guidance regarding effective dosages for treatment in accordance with the present disclosure. In terms of treatment protocols, it should be appreciated that the dosage to be administered will depend on several factors, including the particular agent that is administered, the route administered, the condition of the particular patient, etc. Determination of these parameters are well within the skill of the art. These considerations, as well as effective formulations and administration procedures are well known in the art and are described in standard textbooks.

The compositions provided herein may be administered alone, or in combination with one or more other active ingredients.

The pharmaceutical compositions provided herein may be formulated in various dosage forms for oral, parenteral, buccal, intranasal, epidural, sublingual, pulmonary, local, rectal, transdermal, or topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy, supra; Modified-Release Drug Deliver Technology,* Rathbone et al., Eds., Drugs and the Pharmaceutical Science, Marcel Dekker, Inc.: New York, N.Y., 2002; Vol. 126).

In various embodiments, the pharmaceutical compositions provided herein may be provided in solid, semisolid, or liquid dosage forms for oral administration As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

In further embodiments, the pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The liquid, semisolid, and solid dosage forms provided herein may be encapsulated in a capsule. Suitable liquid and semisolid dosage forms include solutions and suspensions in propylene carbonate, vegetable oils, or triglycerides.

In other embodiments, the pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

In various embodiments, the pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient can also be modified by varying the particle size of the active ingredient(s). Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

In other embodiments, the pharmaceutical compositions provided herein in an immediate release dosage form are capable of releasing not less than 75% of the therapeutically active ingredient or combination and/or meet the disintegration or dissolution requirements for immediate release tablets of the particular therapeutic agents or combination included in the tablet core, as set forth in USP XXII, 1990 (The United States Pharmacopeia.).

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The examples and preparations provided below further illustrate and exemplify the compounds of the present disclosure and methods of preparing such compounds. It is to be understood that the scope of the present disclosure is not limited in any way by the scope of the following examples and preparations.

EXAMPLES

The present disclosure is further illustrated by the following examples, which should not be construed as limiting in any way. The experimental procedures to generate the data shown are discussed in more detail below. The disclosure has been described in an illustrative manner, and it is to be understood that the terminology used is intended to be in the nature of description rather than of limitation.

General Experimental Details
Instrument and Methodology Details
X-Ray Powder Diffraction (XRPD)

X-Ray Powder Diffraction patterns were collected on a Bruker AXS C2 GADDS diffractometer or a Bruker D8 diffractometer.

X-Ray Powder Diffraction patterns collected on a Bruker AXS C2 GADDS diffractometer were performed using Cu Ka radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. The beam divergence, i.e. the effective size of the X-ray beam on the sample, was approximately 4 mm. A θ-θ continuous scan mode was employed with a sample-detector distance of 20 cm which gives an effective 2θ range of 3.2-29.7°. Typically the sample would be exposed to the X-ray beam for 120 seconds. The software used for data collection was GADDS for WNT 4.1.16 and the data were analysed and presented using Diffrac Plus EVA v 9.0.0.2 or v 13.0.0.2. Samples run under ambient conditions were prepared as flat plate specimens using powder as received without grinding. Approximately 1-2 mg of the sample was lightly pressed on a glass slide to obtain a flat surface.

X-Ray Powder Diffraction patterns collected on a Bruker D8 diffractometer were performed using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.5.0 and the data were analysed and presented using Diffrac Plus EVA v 11,0.0.2 or v 13.0.0.2. Samples were run under ambient conditions as flat plate specimens using powder as received. Approximately 20 mg of the sample was gently packed into a cavity cut into polished, zero-background (510) silicon wafer. The sample was rotated in its own plane during analysis. The details of the data collection are:

Angular range: 2 to 42°2θ
Step size: 0.05°2θ
Collection time: 0.5 s·step$^{-1}$

Single Crystal X-Ray Diffraction (SCXRD)

Data were collected on a Bruker AXS 1K SMART CCD diffractometer equipped with an Oxford Cryosystems Cryostream cooling device. Structures were solved using either the SHELXS or SHELXD programs and refined with the SHELXL program as part of the Bruker AXS SHELXTL suite. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Nuclear Magnetic Resonance (NMR)

$^1$H NMR spectra were collected on a Bruker 400 MHz instrument equipped with an auto-sampler and controlled by a DRX400 console. Automated experiments were acquired using ICON-NMR v4.0.4 (build 1) running with Topspin v 1.3 (patch level 8) using the standard Bruker loaded experiments. For non-routine spectroscopy, data were acquired through the use of Topspin alone. Samples were prepared in d6-DMSO, unless otherwise stated. Off-line analysis was carried out using ACD SpecManager v 9.09 (build 7703).

Differential Scanning Calorimetry (DSC)

DSC data were collected on a TA Instruments Q2000 equipped with a 50 position auto-sampler. The calibration for thermal capacity was carried out using sapphire and the calibration for energy and temperature was carried out using certified indium. Typically 0.5-3 mg of each sample, in a pin-holed aluminium pan, was heated at 10° C.·min$^{-1}$ from 25° C. to 250° C. A purge of dry nitrogen at 50 was maintained over the sample. The instrument control software was Advantage for Q Series v2.8.0.392 and Thermal Advantage v4.8.3 and the data were analysed using Universal Analysis v4.3A.

Thermo-Gravimetric Analysis (TGA)

TGA data were collected on a TA Instruments Q500 TGA, equipped with a 16 position auto-sampler. The instrument was temperature calibrated using certified Alumel. Typically 5-15 mg of each sample was loaded onto a pre-tared platinum crucible and aluminium DSC pan, and was heated at 10° C.·min$^{-1}$ from ambient temperature to 250° C. A nitrogen purge at 60 was maintained over the sample. The instrument control software was Advantage for Q Series v2.8.0.392 and Thermal Advantage v4.8.3

Polarised Light Microscopy (PLM)

Samples were studied on a Leica LM/DM polarised light microscope with a digital video camera for image capture. A small amount of each sample was placed on a glass slide, mounted in immersion oil and covered with a glass slip, the individual particles being separated as well as possible. The sample was viewed with appropriate magnification and partially polarised light, coupled to a X false-colour filter.

Gravimetric Vapour Sorption (GVS)

Sorption isotherms were obtained using a SMS DVS Intrinsic moisture sorption analyser, controlled by SMS Analysis Suite software. The sample temperature was maintained at 25° C. by the instrument controls. The humidity was controlled by mixing streams of dry and wet nitrogen, with a total flow rate of 200 ml.min$^{-1}$. The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg). Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0.5-90% RH range. The sample was recovered after completion of the isotherm and re-analysed by XRPD.

TABLE 1

Method Parameters for SMS DVS Intrinsic Experiments

| Parameters | Values |
|---|---|
| Adsorption-Scan 1 | 40-90 |
| Desorption/Adsorption-Scan 2 | 85-Dry, Dry-40 |
| Intervals (% RH) | 10 |
| Number of Scans | 2 |
| Flow rate (ml · min$^{-1}$) | 200 |
| Temperature (° C.) | 25 |
| Stability (° C. · min$^{-1}$) | 0.2 |
| Sorption Time (hours) | 6 hour time out |

Thermodynamic Aqueous Solubility

Aqueous solubility was determined by suspending sufficient compound in water to give a maximum final concentration of 210 mg·ml$^{-1}$ of the parent free-form of the compound. The suspension was equilibrated at 25° C. for 24 hours then the pH was measured. The suspension was then filtered through a glass fibre C filter into a 96 well plate. The filtrate was then diluted by a factor of 101. Quantitation was by HPLC with reference to a standard solution of approximately 0.1 mg·ml$^{-1}$. in DMSO. Different volumes of the standard, diluted and undiluted sample solutions were injected. The solubility was calculated using the peak areas determined by integration of the peak found at the same retention time as the principal peak in the standard injection.

TABLE 2

HPLC Method Parameters for Solubility Measurements

| | |
|---|---|
| Type of method: | Reverse phase with gradient elution |
| Column: | Phenomenex Luna, C18 (2) |
| | 5 pm 50 × 4.6 mm |
| Column Temperature (° C.): | 25 |

TABLE 2-continued

HPLC Method Parameters for Solubility Measurements

| | |
|---|---|
| Standard Injections (pl): | 1, 2, 3, 5, 7, 10 |
| Test Injections (pl): | 1, 2, 3, 10, 20, 50 |
| Detection: Wavelength, Bandwidth (nm): | 260 ,80 |
| Flow Rate (ml · min$^{-1}$): | 2 |
| Phase A: | 0.1% TFA in water |
| Phase B: | 0.085% TFA in acetonitrile |

| Timetable: | Time (min) | % Phase A | % Phase B |
|---|---|---|---|
| | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Analysis was performed on an Agilent HP1 100 series system equipped with a diode array detector and using ChemStation software vB.02.01-SR1.

Chemical Purity Determination by HPLC

Purity analysis was performed on an Agilent HP1 100 series system equipped with a diode array detector and using ChemStation software vB.02.01-SR1.

TABLE 3

HPLC Method Parameters for Chemical Purity Determinations

| | |
|---|---|
| Sample Preparation: | 0.6-3 mg/ml in acetonitrile:water 1:1 v/v |
| Column: | Phenomenex Luna C18 (2), 150 × 4.6 mm, 5 μm |
| Column Temperature (° C.): | 25 |
| Injection (pl): | 1-5 |
| Detection: Wavelength, Bandwidth( nm): | 255, 90 |
| Flow Rate (ml · min$^{-1}$): | 1 |
| Phase A: | 0.1% TFA in water |
| Phase B: | 0.085% TFA in acetonitrile |

| Timetable: | Time (min) | % Phase A | % Phase |
|---|---|---|---|
| | 0 | 95 | 5 |
| | 25 | 5 | 95 |
| | 25.2 | 95 | 5 |
| | 30 | 95 | 5 |

Ion Chromatography (IC)

Data were collected on a Metrohm 861 Advanced Compact IC (for anions) using IC Net software v2.3. Accurately weighed samples were prepared as stock solutions in DMSO and diluted 1:9 with either DMSO or water prior to testing. Quantification was achieved by comparison with standard solutions of known concentration of the ion being analysed.

TABLE 4

HPLC Method Parameters for Anion Chromatography

| | |
|---|---|
| Type of method | Anion exchange |
| Column: | Metrosep A Supp 5-250 (4.0 × 250 mm) |
| Column Temperature (° C.): | Ambient |
| Injection (μl): | 20 |
| Detection: | Conductivity detector |
| Flow Rate (ml · min$^{-1}$): | 0.7 |
| Eluent: | 3.2 mM sodium carbonate, 1.0 mM sodium hydrogen carbonate in 5% aqueous acetone. | pKa Determination and Prediction

Data were collected on a Sirius GlpKa instrument with a D-PAS attachment. Measurements were made at 25° C. in aqueous solution by UV and in methanol water mixtures by potentiometry. The titration media was ionic-strength adjusted (ISA) with 0.15 M KCl (aq). The values found in the methanol water mixtures were corrected to 0% co-solvent via a Yasuda-Shedlovsky extrapolation. The data were refined using Refinement Pro software v2.2. Prediction of pKa values was made using ACD pKa prediction software v12.

Log P Determination

Data were collected by potentiometric titration on a Sirius GlpKa instrument using three ratios of octanol:ionic-strength adjusted (ISA) water to generate Log P, Log Pion, and Log D values. The data were refined using Refinement Pro software v2.2. Prediction of Log P values was made using ACD v12 software.

Example 1

Processes for the synthesis of 14-methyl-20-Oxa-5,7, 14,27-tetraazatetracyclo-[19.3.1.12,6.18,12]heptacosa-1(25),2,4,6,8,10,12(26),16,21,23-decaene (Compound I)

The synthesis of Compound I free base has been reported in WO 2007/058628 which is incorporated by reference in its entirety. Additional synthetic routes to Compound I are presented below.

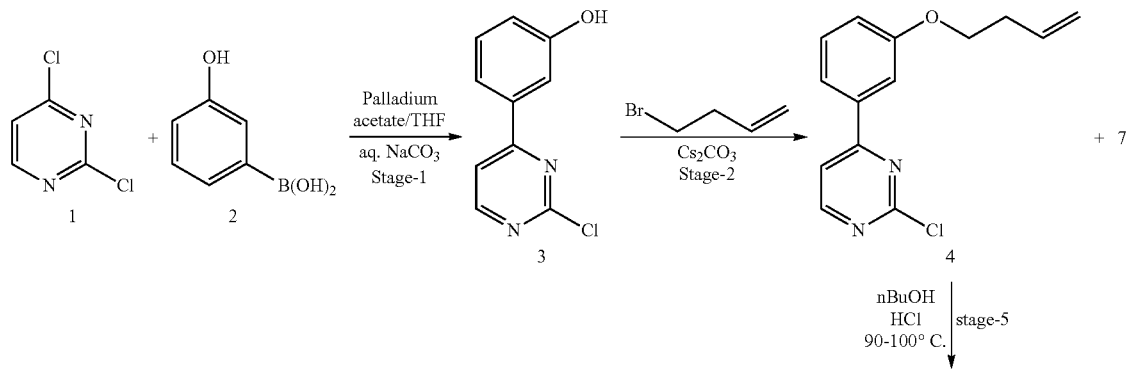

Scheme 1 - Synthesis of Compound I

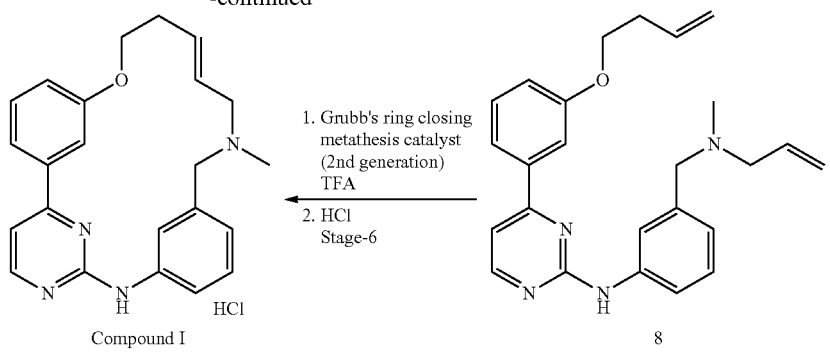

As illustrated in Scheme 1, 2,4-dichloropyrimidine (1) was subjected to a palladium (II)-mediated cross-coupling reaction with 3-hydroxyphenylboronic acid (2) to give the 4-substituted pyrimidine 3. Alkylation with 1-bromo-3-butene followed by condensation with aniline 7 afforded the tricyclic alkene 8. Subjecting compound 8 to the ring closing metathesis reaction provided Compound I which was isolated as the hydrochloride salt.

Scheme 2 - Synthesis of Intermediate 7

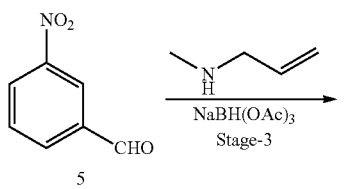

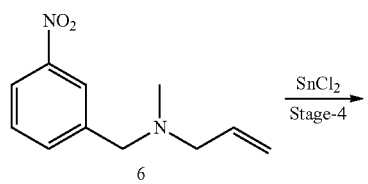

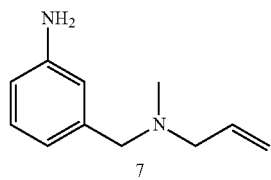

Scheme 2 illustrates the synthesis of aniline 7. 3-Nitrobenzaldehyde is subjected to a reductive amination with N-methylallylamine to give amine 6. Reduction of the nitro group with SnCl$_2$ afforded aniline 7.

Scheme 3 - Synthesis of Compound I

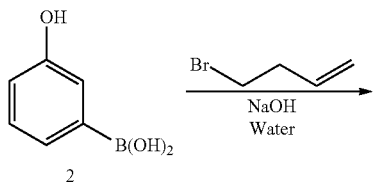

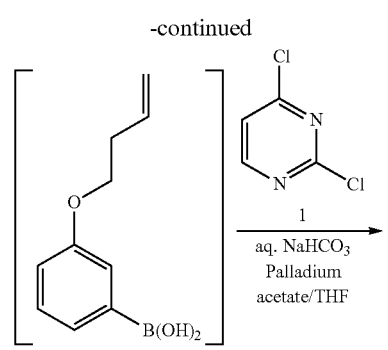

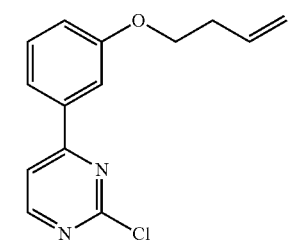

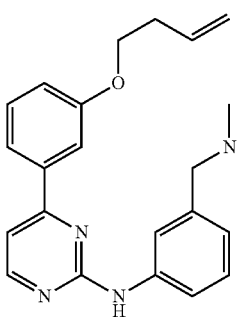

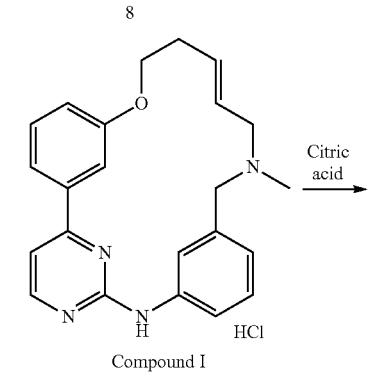

-continued

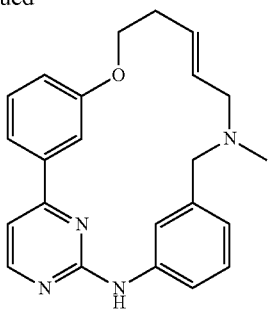

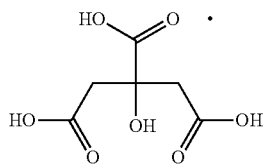

An alternative synthesis of Compound I is presented in Scheme 3, alkylation of 3-hydroxyphenylboronic acid with 1-bromo-3-butene followed by palladium (II)-mediated cross-coupling reaction with 2,4-dichloropyrimidine 2-chloropyrimidine compound 4. Condensation with aniline 7 afforded tricyclic diene 8. Subjecting compound 8 to the ring closing metathesis reaction provided Compound I which was isolated as the citrate salt.

Example 2

Characterization of 14-methyl-20-Oxa-5,7,14,27-tetraazatetracyclo-[19.3.1.12,6.18,12]heptacosa-1(25),2,4,6,8,10,12(26),16,21,23-decaene (Compound I)

The Table below is a summary of the characterisation of the free base of compound I.

TABLE 5

Summary of Characterisation of the free base of Compound I

| Experiment | Comments |
| --- | --- |
| $^1$H-NMR (400 MHz, DMSO, d6) | The $^1$H-NMR spectrum was consistent with the proposed structure. |
| HPLC purity | 96.8%-3 main impurities were measured at 2.01; 0.51 and 0.35% area. |
| XRPD stability (40° C./75% R.H.) | The material was crystalline and the diffractogram was of Pattern 1 of the free base. No changes were observed in the humidity chamber after the sample was stored at 40° C. and 75% R.H. for 6 weeks. |
| HPLC Purity post stability (40° C./75% R.H.) | After 6 weeks in the humidity chamber, the purity of Compound I was measured at 97.0% area. Four main impurities were measured at 1.87; 0.37 and 0.30% area. |
| Optical Microscopy | The material displays birefringence under polarised light; the particles have needle-like morphology. |
| TGA/DSC @ 10° C./min | The melt of the product was recorded at 181° C. and was associated with a small mass loss in TGA of 0.24% w/w (before degradation at circa 250° C.). A small endothermic shoulder was detected which could be associated with the presence of a crystalline chemical impurity, another crystalline phase of compound I free base or is due to the release of residual solvent. |
| GVS @ 25° C. | GVS analysis was carried out at 25° C. No hydration phenomenon was observed and the |

TABLE 5-continued

Summary of Characterisation of the free base of Compound I

| Experiment | Comments |
| --- | --- |
| | isotherms showed less than 7.5 wt % difference between 0 and 90% relative humidity. No changes in the XRPD pattern (pattern 1 of the free base) were detected after the experiment. |
| Thermodynamic stability in water | Insoluble <0.001 mg/mL, final pH = 8.9 (the material floats on the surface of the water). |

Figure 26:
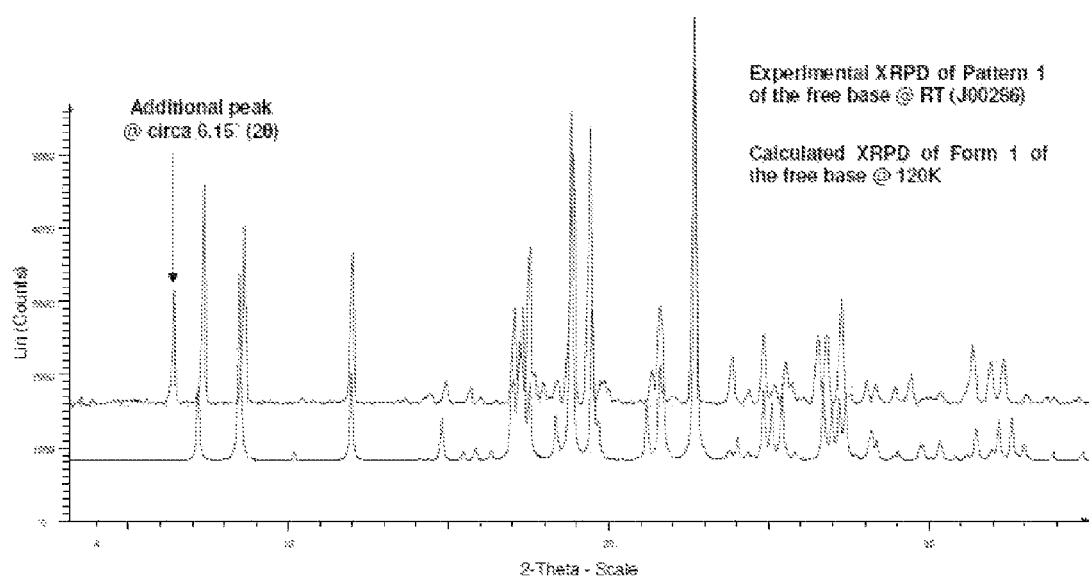
FIG. 26 shows the comparison between the experimental XPRD pattern 1 of the free base and the calculated XPRD pattern of form 1, wherein the upper trace is the experimental XRPD and the lower trace is the calculated XRPD.

Additionally to these characterisation data, single crystals were obtained by slow evaporation of a free base solution in TI-IF at RT. The crystal structure of anhydrous Form 1 of the free base was solved and the comparison between the simulated XRPD diffractogram and the experimental Pattern 1 of the free base showed a good match, except one additional peak at circa 6.2° (2θ) which could be due to a crystalline impurity (see the superimposition of simulated and experimental XRPD patterns in FIG. 26).

Figure 2:
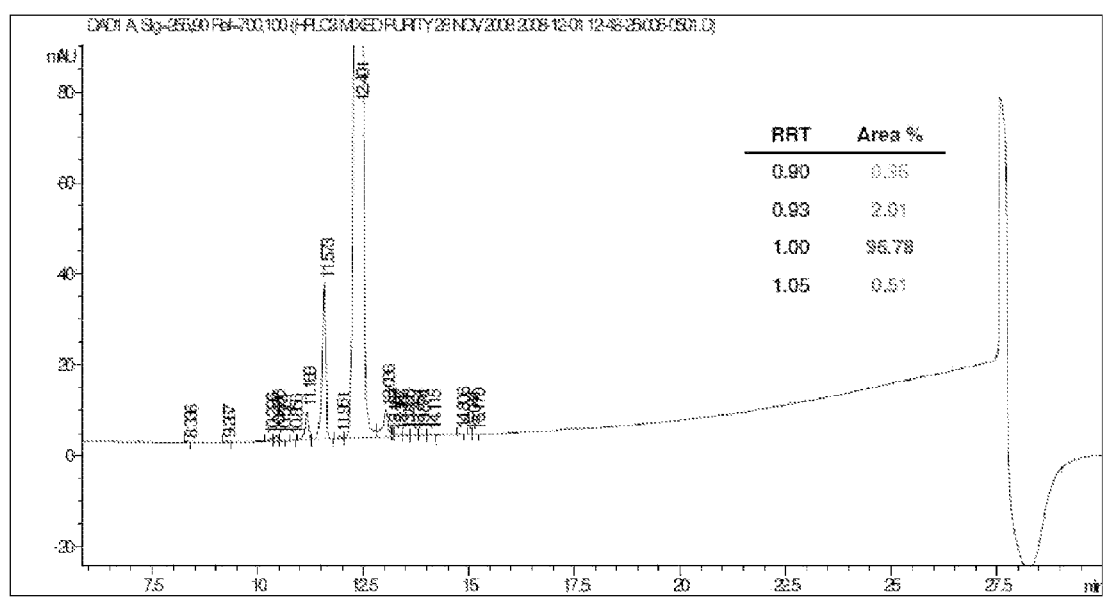
FIG. 2 shows the HPLC chromatogram of Compound I.
Figure 3:
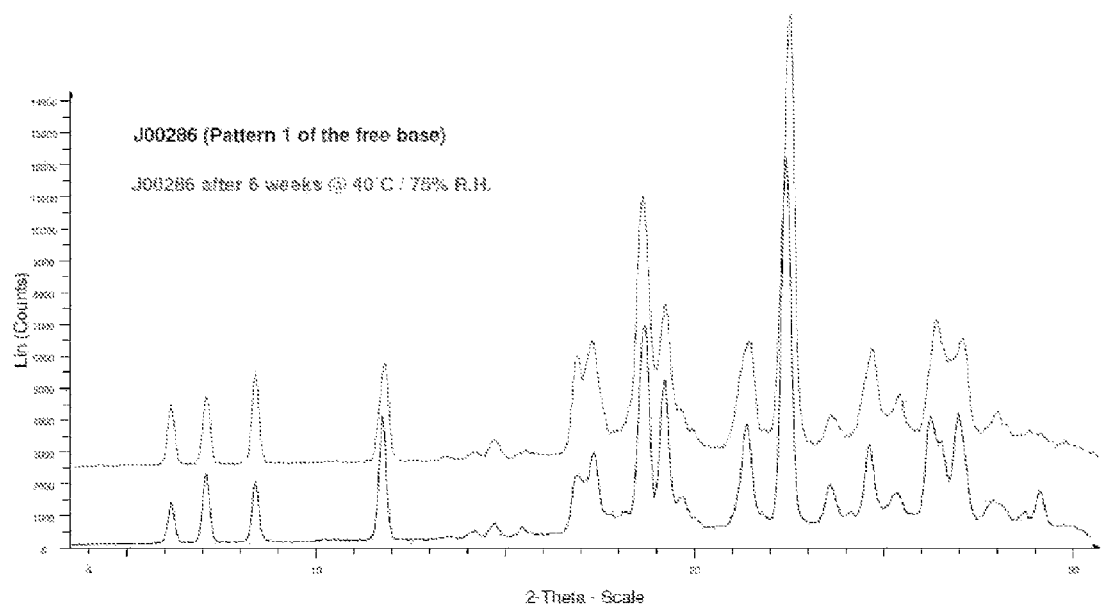
FIG. 3 shows a XRPD of Compound I after stability study (40° C./75% R.H.), wherein the upper trace represents J00286 after 6 weeks at 40° C./75% relative humidity and the lower trace represents J00286 (Pattern 1 of the free base)
Figure 4:
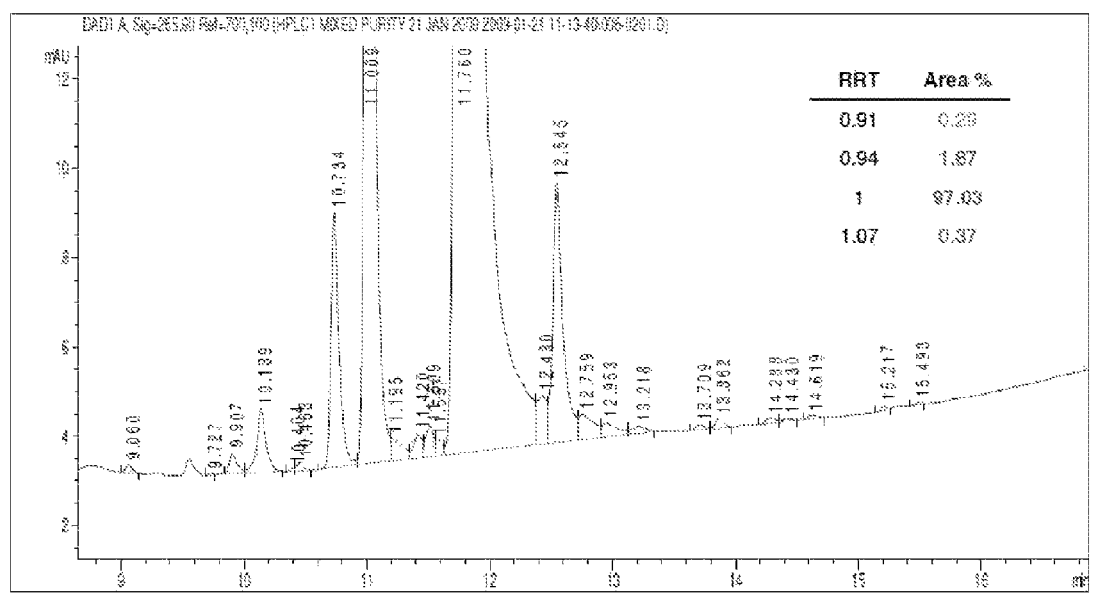
FIG. 4 shows a HPLC chromatogram of Compound I post-stability study.
Figure 5:
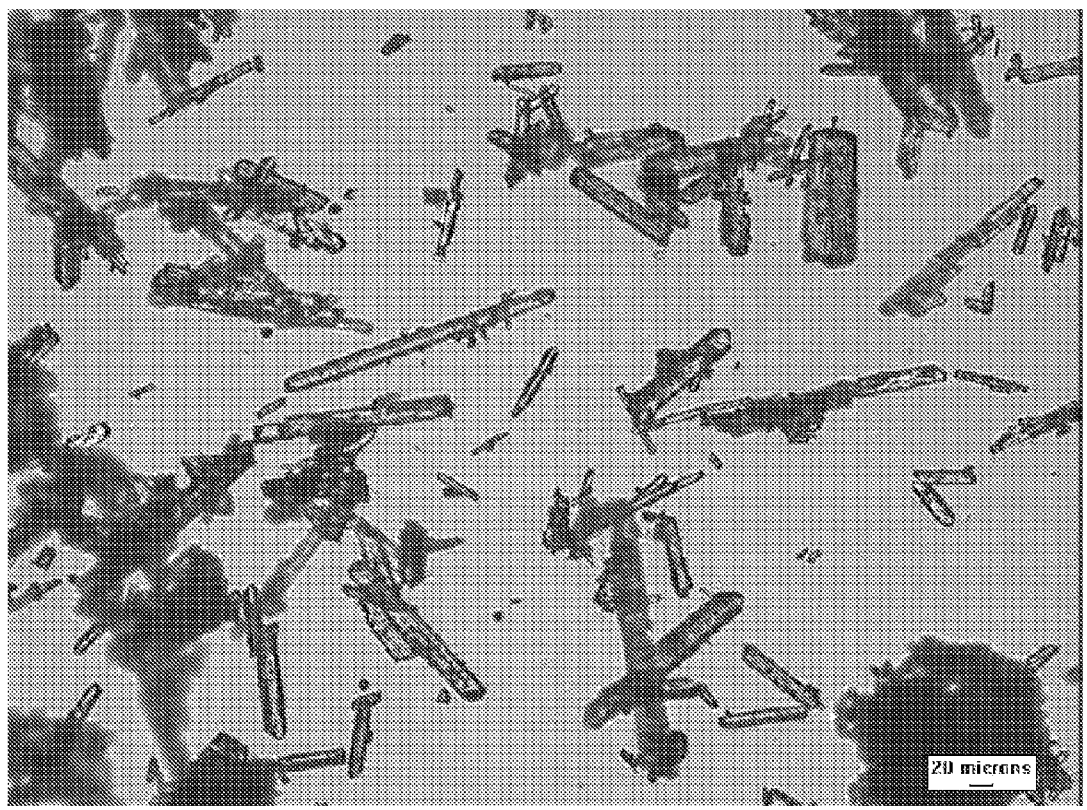
FIG. 5 shows an optical microscopy photograph of Compound I.
Figure 6:
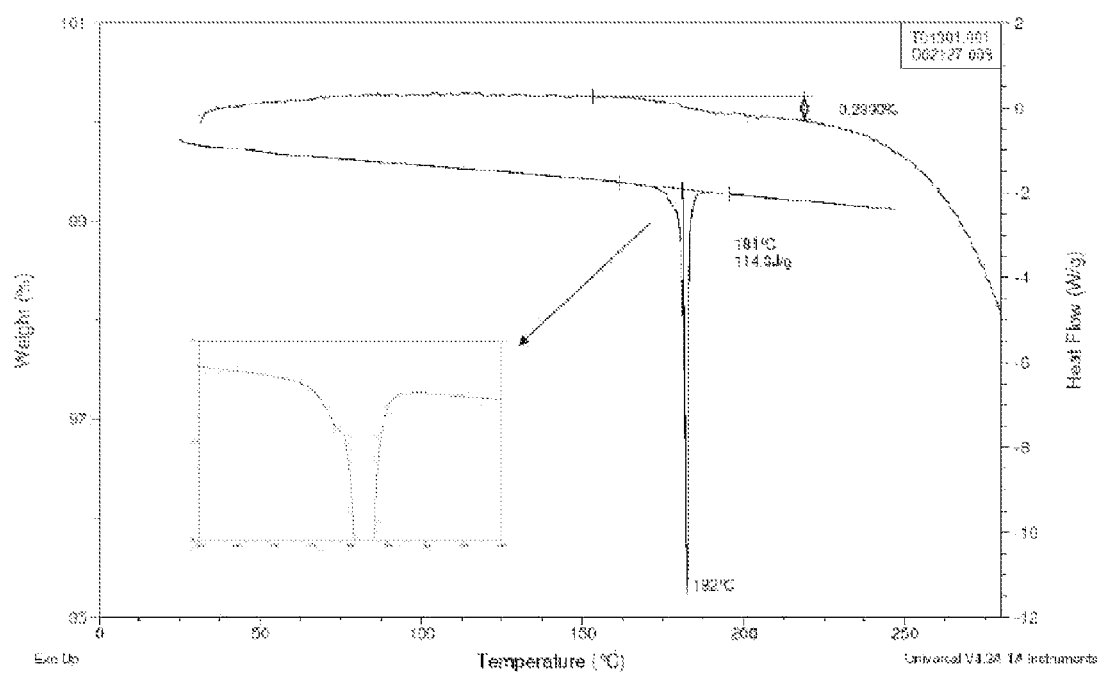
FIG. 6 the recording of the TGA/DSC of Compound I at 10° C./min, wherein the upper trace represents the percent weight as a function of temperature and the lower trace represents the heat flow as a function of temperature.
Figure 7:
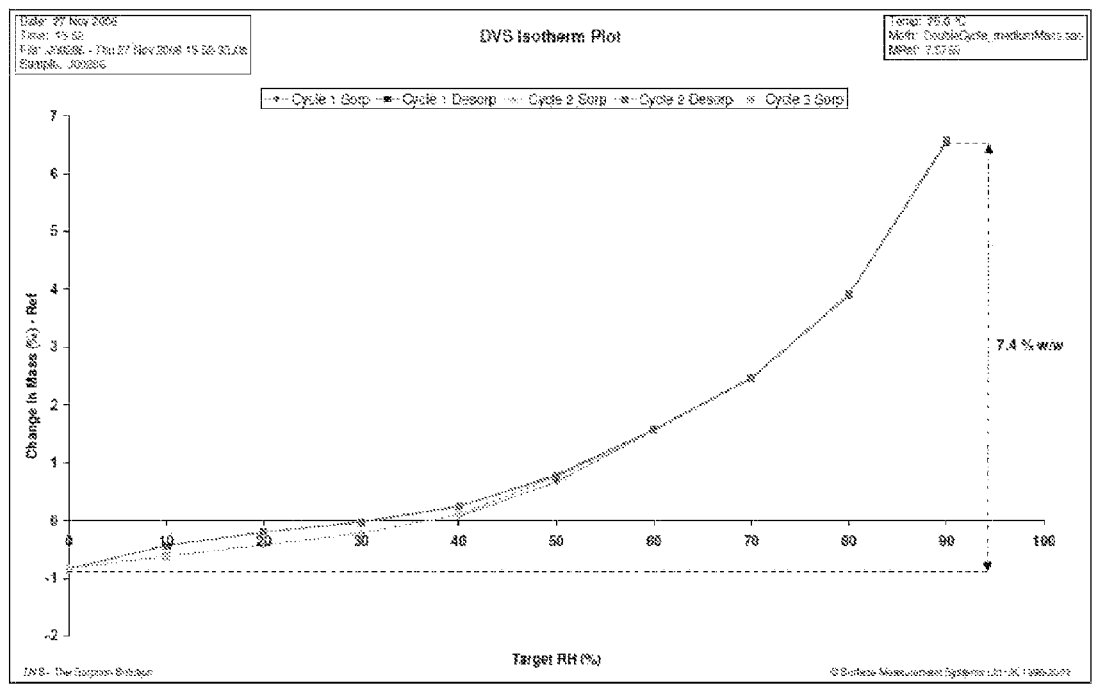
Figure 8:
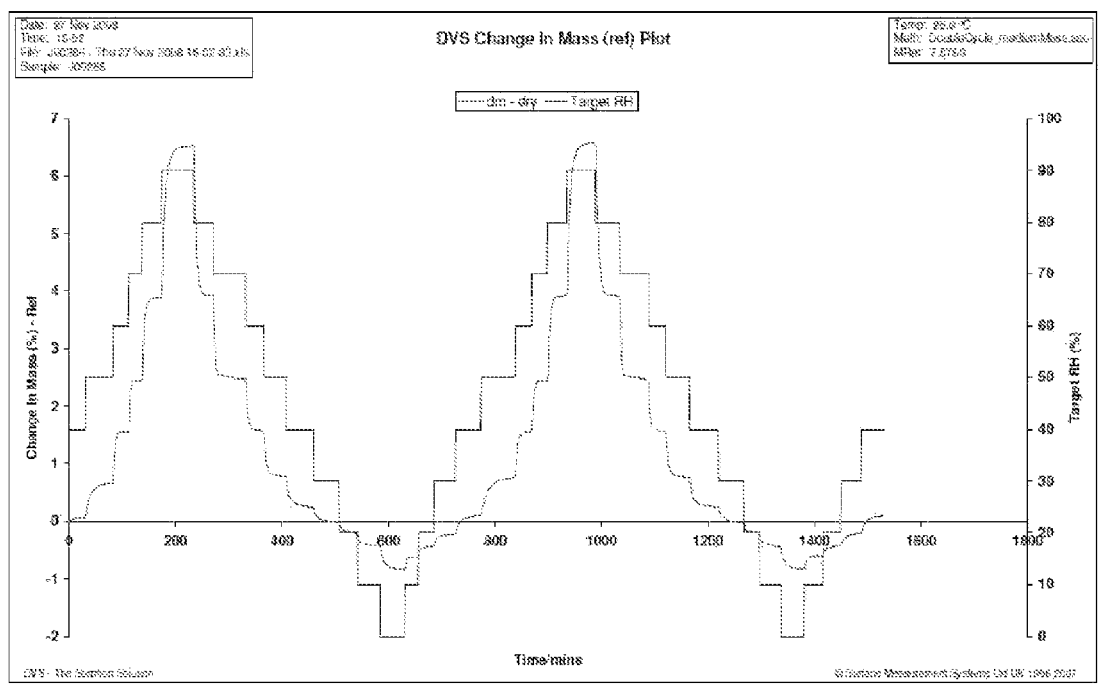
Figure 9:
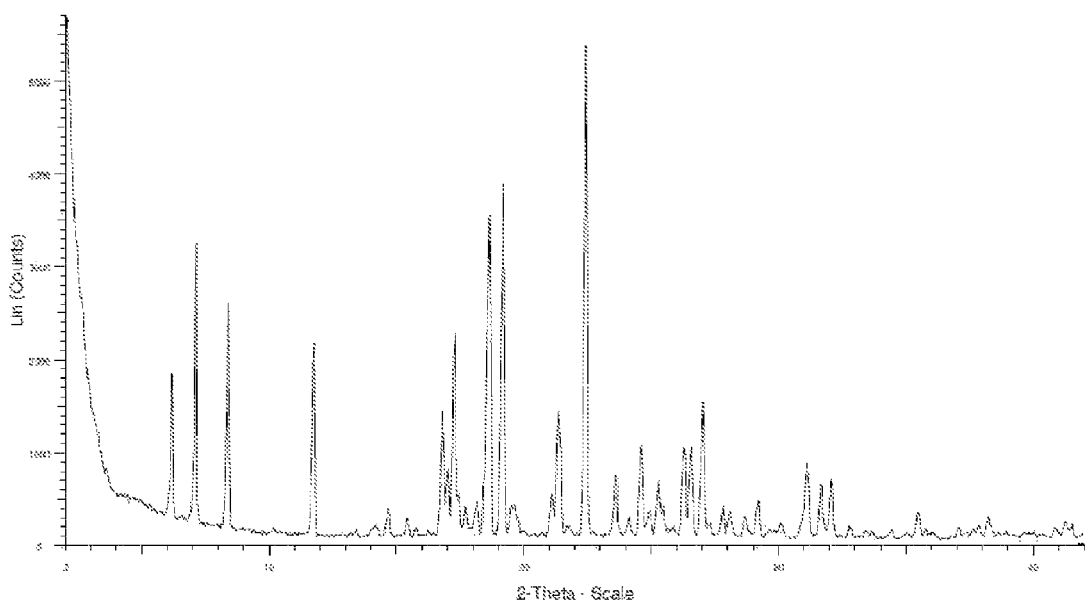
FIG. 9 shows a high resolution XRPD of Compound I.
Figure 10:
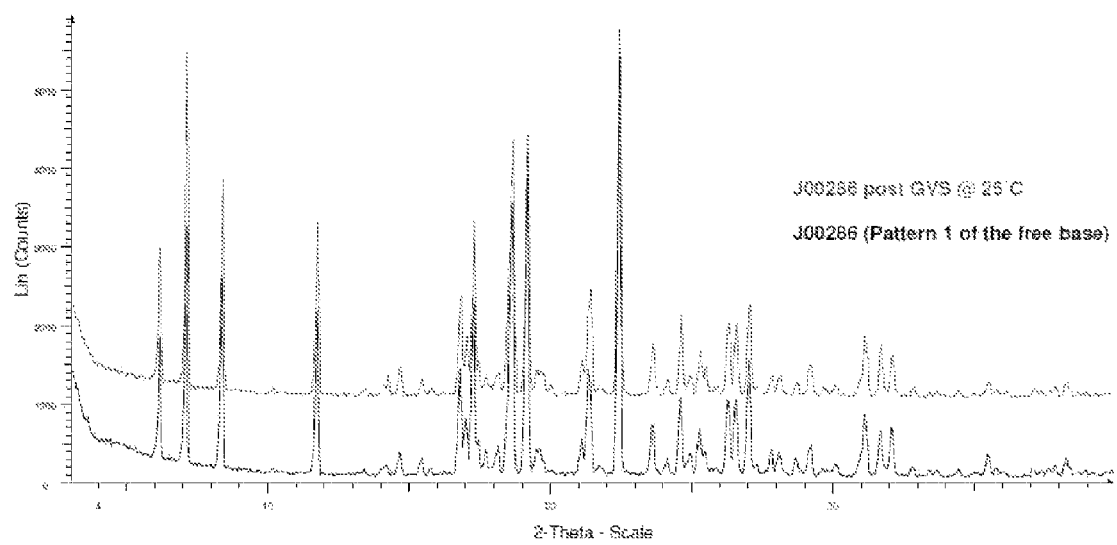
FIG. 10 shows a XRPD of Compound I after GVS study, wherein the upper trace represents J00286 post GVS at 25° C. and the lower trace represents J00286 (Pattern 1 of the free base)

The $^1$HNMR spectrum of Compound I is given in FIG. 1.
The HPLC chromatogram of Compound I is given in FIG. 2.
A XRPD of Compound I after stability study (40° C./75% R.H.) is illustrated in FIG. 3.
A HPLC chromatogram of Compound I post-stability study is given in FIG. 4.
An optical microscopy photograph of Compound I is provided in FIG. 5.
The recording of the TGA/DSC @ 10° C./min is provided in FIG. 6.
The GVS at 25° C. curves are provided in FIGS. 7 and 8.
A high resolution XRPD of Compound I is provided in FIG. 9.
A XRPD of Compound I after GVS study is illustrated in FIG. 10

Example 2a pKa and logP Determination of 14-methyl-20-Oxa-5,7,14,27-tetraazatetracyclo-[19.3.1.12,6.18,12]heptacosa-1(25),2,4,6,8,10,12(26),16,21,23-decaene (Compound I)

pKa and logP determinations were performed as described above. The pKa values for Compound I were calculated and measured, and the correlation between both values was in good agreement.

| | |
| --- | --- |
| ACD (V9) Predicted LogP = | 4.0 |
| Measured LogP = | 4.72 |
| Measured LogP$_{ion}$ = | 1.14 |
| Measured LogD$_{7.4}$ = | 3.34 |

Example 3

Salt Screen

A preliminary screen of solvents for crystallization with hydrochloric acid and tartaric acid indicated that tetrahydrofuran, methyl ethyl ketone (MEK) and water:ethanol (1:1/v:v) were good solvents for obtaining crystalline products. Taking in consideration the pKa values, a number of acids were selected to carry out the salt screen. These acids are shown in the Table 6.

TABLE 6

Acids Selected for Salt Screen

| Acid | Class | Concentration | pKa1 | pKa2 | pKa3 |
|---|---|---|---|---|---|
| Hydrochloric acid | 1 | 1 M in THF | −6.10 | | |
| Sulphuric acid | 1 | 1 M in THF | −3.00 | 1.92 | |
| Methane sulphonic acid | 2 | 1 M in THF | −1.20 | | |
| Benzene sulphonic acid | 2 | 1 M in THF | 0.70 | | |
| Maleic acid | 1 | 1 M in THF | 1.92 | 6.23 | |
| Phosphoric acid | 1 | 1 M in THF | 1.96 | 7.12 | 12.32 |
| L-glutamic acid | 1 | N/A | 2.19 | 4.25 | |
| L-tartaric acid | 1 | 1 M in THF | 3.02 | 4.36 | |
| Fumaric acid | 1 | 0.5 M in THF/methanol | 3.03 | 4.38 | |
| Citric acid | 1 | 1 M in THF | 3.13 | 4.76 | 6.40 |
| L-Malic acid | 1 | 1 M in THF | 3.46 | 5.10 | |
| L-lactic acid | 1 | 1 M in THF | 3.86 | | |
| Succinic acid | 1 | 1 M in THF | 4.21 | 5.64 | |
| Acetic acid | 1 | 1 M in THF | 4.76 | | |

No salt formation and/or no crystalline solids were obtained for the samples containing 1 eq. of phosphoric acid, L-glutamic acid, L-lactic acid and acetic acid.

The free base (50 mg, 0.134 mmol) was weighted into 2 cm$^3$ vials and the appropriate solvent was added; 15 volumes in THF and 50 volumes in MEK and water:ethanol mixture. The samples were then warmed, under shaking, up to 50° C. for 2 hours to obtain homogeneous solutions.

Each sample was then treated with 1 eq. of the corresponding acid (or 2 eq. for the HCl salt) and subjected to a series of heat-cool cycles from RT to 50° C. (8 hour cycles). After 12 hours of maturation, the samples which did not yield any solid were cooled down 4° C.

After 2 days, the solids were isolated by filtration under vacuum at RT to be characterised by XRPD analysis. Each new crystalline solid phase detected was characterised by $^1$H NMR and TGA-DSC analyses in order to determine if salt formation had occurred and whether the material was a solvate. At this stage, each salt identified was then analysed by HPLC to determine the chemical purity prior to being stored in the humidity chamber (40° C./75% R.H.) to assess its stability. The experimental results are summarised in Table 7.

TABLE 7

Summary of Salt Screen

| Acid | XPRD pattern | TGA-DSC at 10° C./min | XPRD stability after 40° C./75% RH 2 weeks |
|---|---|---|---|
| Hydrochloric acid | HCl pattern 2 | Mass loss 11.19% w/w Dehydration peak at 61° C. Could be trihydrate of monosalt | No change |
| Hydrochloric acid | HCl pattern 6 | Mass loss 2.03% w/w Dehydration peak at 26° C. Melt at 182° C. Could be hemihydrate of monosalt | No change |
| Sulphuric acid | Sulfate pattern 1 | Mass loss 11.63% w/w Dehydration peak at 44° C. Could be trihydrate of hemi-salt | XPRD change to sulfate pattern 2 |
| Methane sulfonic Acid | Mesylate pattern 1 | Not available | XPRD change to mesylate pattern 2 and pattern 3 |
| Benzene sulfonic Acid | Besylate pattern 1 | Mass loss 2.05% w/w Endotherm at 172° C. possible melt | No change |
| Maleic acid | Maleate pattern 1 | Mass loss 6.84% w/w Desolvation peak at 160° C. Could be hemisolvate of MEK | No change |
| Maleic acid | Maleate pattern 2 | Mass loss 7.78% w/w Desolvation peak at 148° C. Could be hemisolvate of THF | No change |
| Fumaric acid | Fumarate pattern 1 | Mass loss 10.90% w/w Desolvation peak at 48° C. Could be trihydrate | No change |
| Fumaric acid | Fumareate pattern 2 | No mass loss Melt at 240° C. | No change |
| Citric acid | Citrate pattern 1 | No mass loss Melt at 191° C. | No change |
| L-Malic acid | Malate pattern 1 | No mass loss Melt at 180° C. | XPRD change to malate pattern 2 |
| Succinic acid | Succinate pattern 1 | Mass loss 9.40% w/w Dehydration peak at 95° C. | No change |

TABLE 7-continued

Summary of Salt Screen

| Acid | XPRD pattern | TGA-DSC at 10° C./min | XPRD stability after 40° C./75% RH 2 weeks |
|---|---|---|---|
| Succinic acid | Succinate pattern 2 | Melt at 169° C. Could be trihydrate Mass loss of 0.72% w/w corresponding to residual solvent. First endotherm at 180° C. Second endotherm at 196° C. | No change |

The salt formation has been successfully obtained for nine counter-ions, during the main screen, resulting in 13 new XRPD patterns as listed below (in addition to Pattern 2 of the hydrochloride):
  HCl Pattern 2 and 6 (crystallised with 2 eq. of HCl)
  Sulfate Pattern 1
  Mesylate Pattern 1
  Besylate Pattern 1
  Maleate Pattern 1 and 2
  Fumarate Pattern 1 and 2
  Citrate Pattern 1 and 2
  Malate Pattern 1
  Succinate Pattern 1 and 2

The most promising results were obtained for the Fumarate Pattern 2 and the Citrate Pattern 1. These mono-salts produced anhydrous crystalline forms with a good yield and with a good crystallinity. Furthermore, both were not sensitive to humidity after 2 weeks (at least) of storage in the humidity chamber at 40° C./75% R.H.

The Besylate Pattern 1 was also an anhydrous form and stable after 2 weeks of storage in the humidity chamber at 40° C./75% R.H. However, its stoichiometry was not clearly determined by integration of the $^1$H NMR signals.

Example 4

Preparation and Characterization of the Citrate Salt of 14-methyl-20-Oxa-5,7,14,27-tetraazatetracyclo-[19.3.1.12,6.18,12]heptacosa-1(25),2,4,6,8,10,12 (26),16,21,23-decaene (Compound I)

The free base of Compound I (650 mg, 1.74 mmol) was dissolved at 50° C. in 50 volumes of MEK (31.25 mL). After homogenisation, the solution was treated with 1 eq. of citric acid (1.745 mL of a 1 M solution in THF). The reaction mixture was then subjected to maturation cycles from room temperature to 50° C. (8 hour cycles) for a 12 hour period. The resulting solid was filtered under vacuum and dried at room temperature to provide 960 mg (97%) of product. XPRD analysis indicates the product is citrate pattern 1 polymorph of Compound I. Citrate Pattern 1 is an anhydrous polymorphic form melting at 191° C. (according the DSC). This salt is also stable in the solid state, at ambient conditions and is not sensitive to humidity (no transformation observed in GVS at 25° C. and after 2 weeks, at least, in the humidity chamber at 40° C./75% R.H.). The aqueous solubility was significantly higher than that of the free base (0.16 mg/mL).

Figure 11:
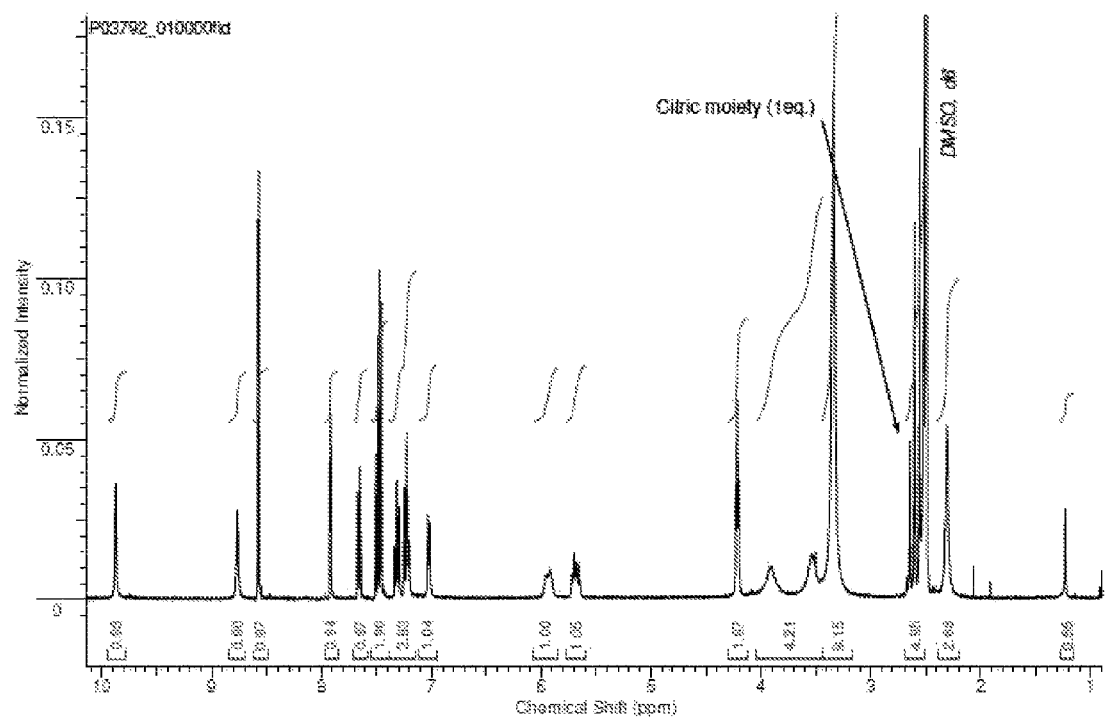
FIG. 11 shows the $^1$H NMR spectrum of the citrate pattern 1 polymorph of Compound I.
Figure 12:
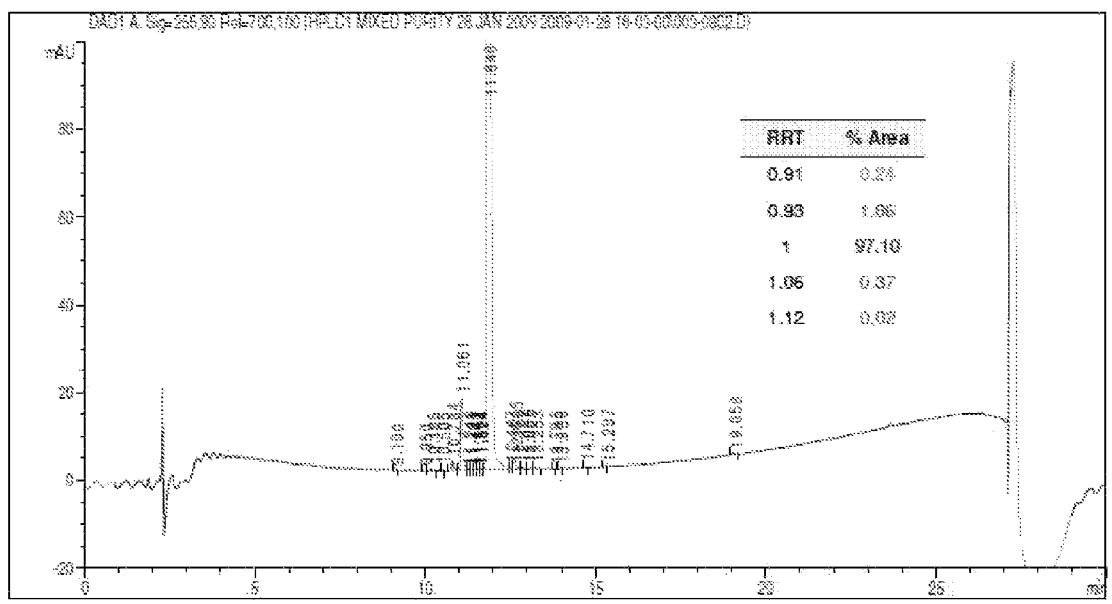
FIG. 12 shows the HPLC chromatogram of the citrate pattern 1 polymorph of Compound I.
Figure 14:
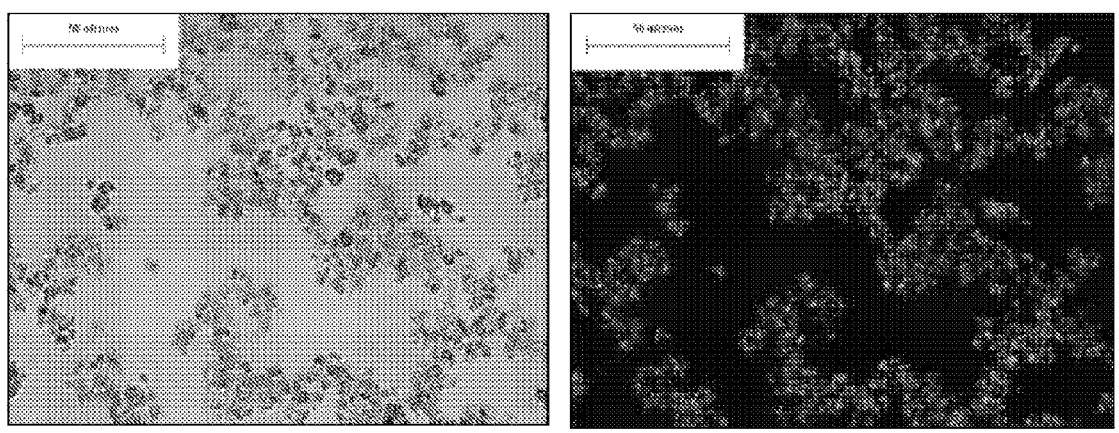
FIG. 14 shows an optical microscopy photograph of the citrate pattern 1 polymorph of Compound I.
Figure 15:
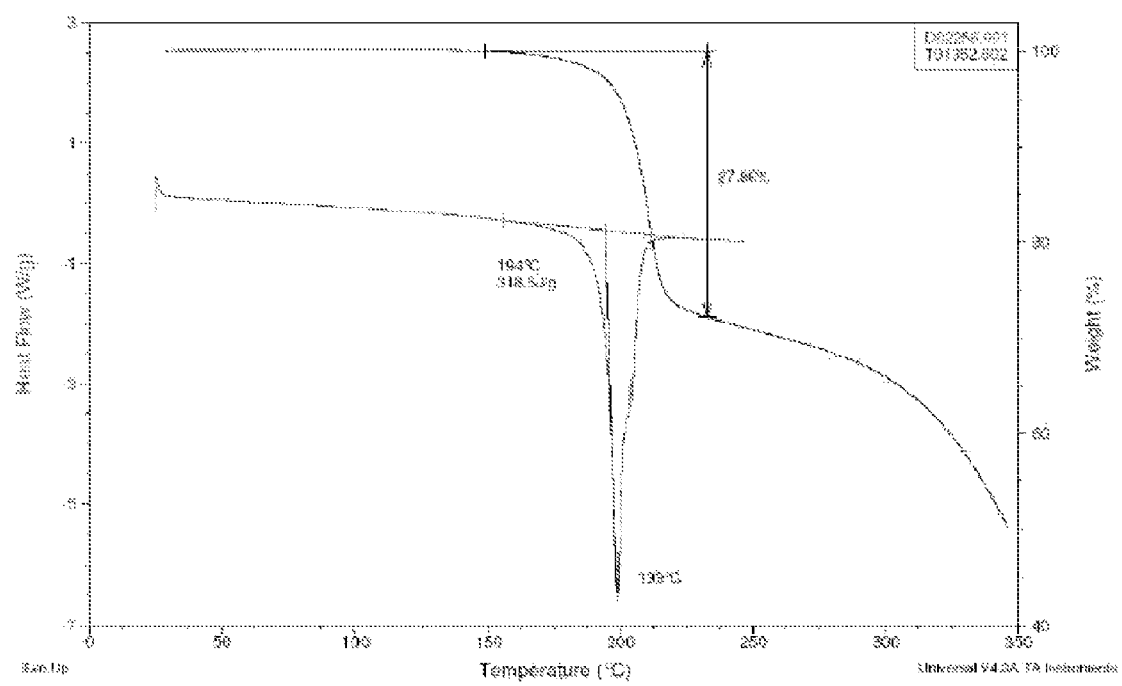
FIG. 15 shows the recording of the TGA/DSC at 10° C./min of the citrate pattern 1 polymorph of Compound I, wherein the upper trace represents the percent weight as a function of temperature and the lower trace represents the heat flow as a function of temperature.
Figure 16:
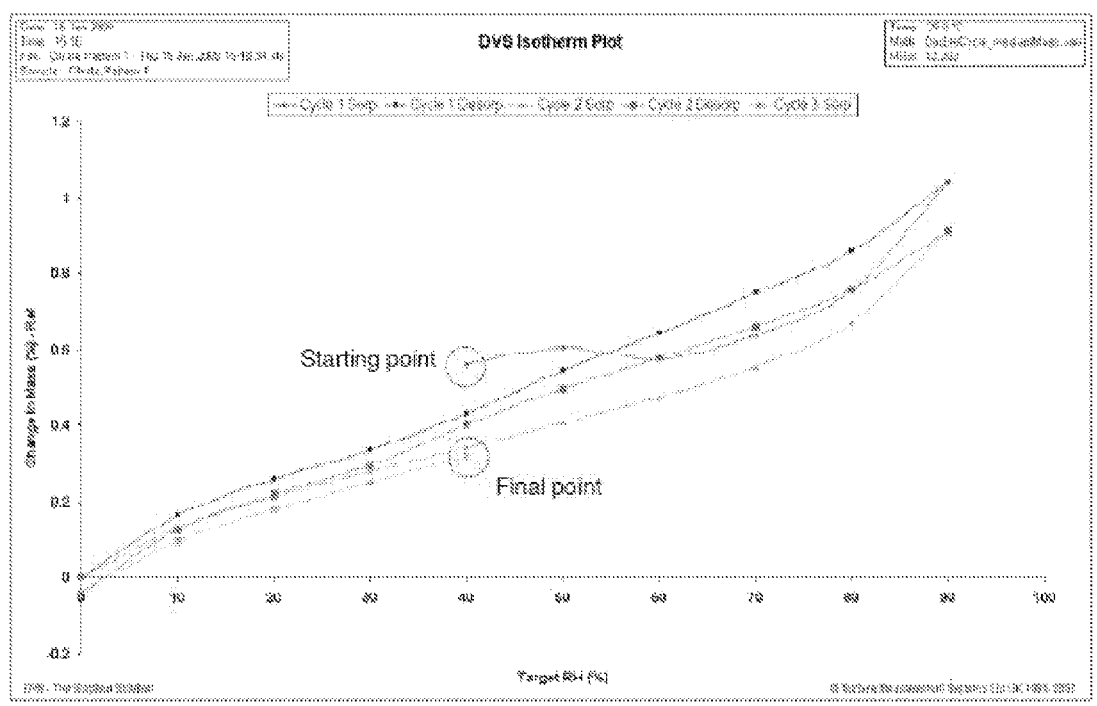
Figure 17:
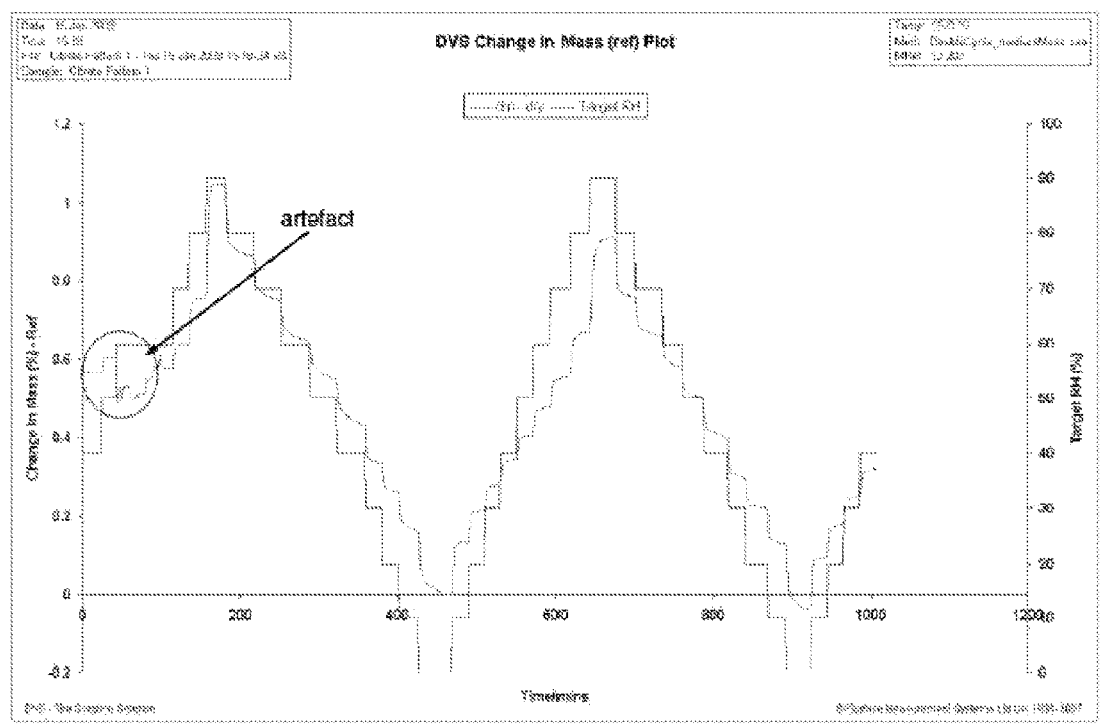
Figure 18:
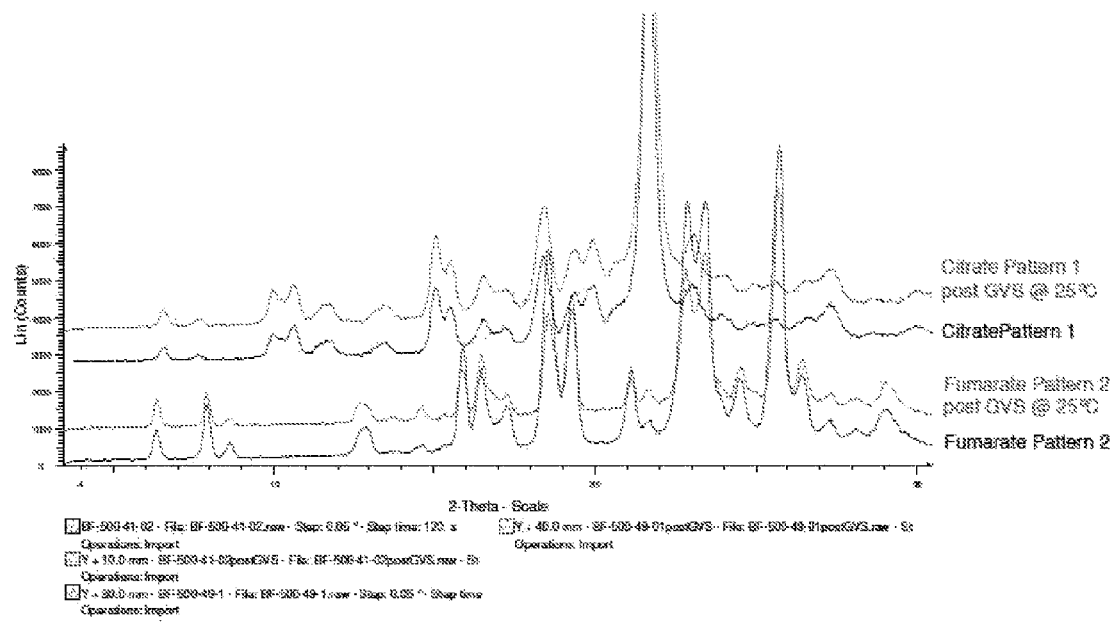
FIG. 18 shows the XRPD of the citrate pattern 1 polymorph and the fumarate pattern 2 polymorph of Compound I after GVS study.

The 1H NMR spectrum of the citrate pattern 1 polymorph of Compound I is given in FIG. 11.
The HPLC chromatogram of the citrate pattern 1 polymorph of Compound I is given in FIG. 12.
A high resolution XRPD of the citrate pattern 1 polymorph of Compound I is provided in FIG. 13.
An optical microscopy photograph of the citrate pattern 1 polymorph of Compound I is provided in FIG. 14.
The recording of the TGA/DSC at 10° C./min of the citrate pattern 1 polymorph of Compound I is provided in FIG. 15.
The GVS at 25° C. curves of the citrate pattern 1 polymorph of Compound I are provided in FIGS. 16 and 17.
A XRPD of the citrate pattern 1 polymorph of Compound I after GVS study is illustrated in FIG. 18.

Table 8 is a summary of the characterisation of the citrate pattern 1 polymorph of Compound I.

TABLE 8

Summary of Characterisation Citrate Pattern 1 of Compound I

| Experiment | Comments |
|---|---|
| $^1$H NMR (400 MHz, DMSO, d6) | The $^1$H NMR spectrum was consistent with the mono-citrate salt. |
| HPLC purity | 97.1% area-3 main impurities were measured at 1.86; 0.37 and 0.24% area. |
| XRPD stability (40° C./75% R.H.) | XPRD of citrate pattern 1 showed good crystallinity, and no change was observed after 2 weeks of storage at 40° C./75% R.H. |
| Optical Microscopy | The material has small agglomerated particles showing birefringence under polarised light. |
| TGA/DSC @ 10° C./min | No mass loss recorded in TGA until the salt dissociation at circa. 200° C. The melt was recorded at 191° C. (onset) in DSC. |
| GVS @ 25° C. | No hydration phenomenon was observed and the isotherms showed less than 1.2 wt % difference between 0 and 90% relative humidity. No changes in the XRPD pattern (citrate pattern 1) were detected after the experiment. |
| Thermodynamic stability in water | 0.16 mg/mL, final pH = 3.94 |

Example 5

Preparation and Characterization of the Fumarate Salt of 14-methyl-20-Oxa-5,7,14,27-tetraazatetracyclo-[19.3.1.12,6.18,12]heptacosa-1(25),2,4,6,8,10,12 (26),16,21,23-decaene (Compound I)

The free base of Compound I (650 mg, 1.74 mmol) was dissolved at 50° C. in 50 volumes of MEK (31.25 mL). After homogenisation, the solution was treated with 1 eq. of fumaric acid (3.490 mL of a 0.5 M solution in THF/methanol). The reaction mixture was then subjected to maturation cycles from room temperature to 50° C. (8 hour cycles) for a 12 hour period. The resulting solid was filtered under vacuum and dried at room temperature to provide 830 mg (97%) of product. XPRD analysis indicates the product is fumarate pattern 2 polymorph of Compound I. Fumarate pattern 2 is an anhydrous polymorphic form melting at 240° C. (according the DSC). Fumarate pattern 2 is stable in the solid state, at ambient conditions (temperature and pressure) and is not sensitive to high level of humidity (no transformation observed in GVS at 25° C. and after 2 weeks, at least, in the humidity chamber at 40° C./75% R.H.). Furthermore, the aqueous solubility was significantly higher than that of the free base (0.029 mg/mL).

Figure 19:
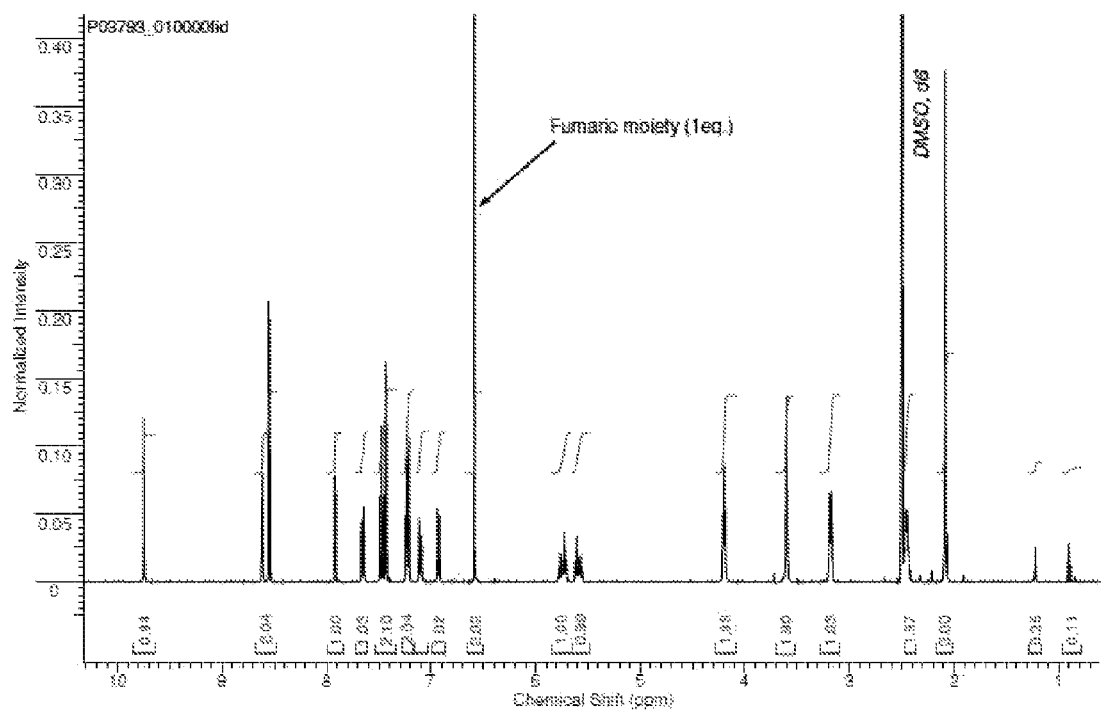
FIG. 19 shows the $^1$H NMR spectrum of the fumarate pattern 2 polymorph of Compound I.

The $^1$H NMR spectrum of the fumarate pattern 2 polymorph of Compound I is given in FIG. 19.

Figure 20:
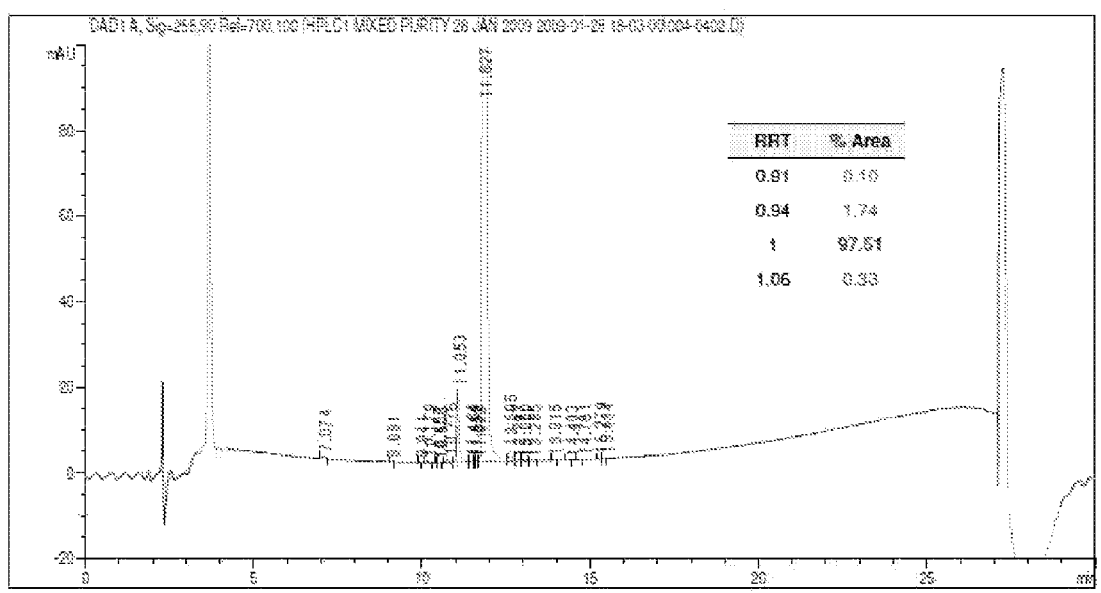
FIG. 20 shows the HPLC chromatogram of the fumarate pattern 2 polymorph of Compound I.

The HPLC chromatogram of the fumarate pattern 2 polymorph of Compound I is given in FIG. 20.

Figure 21:
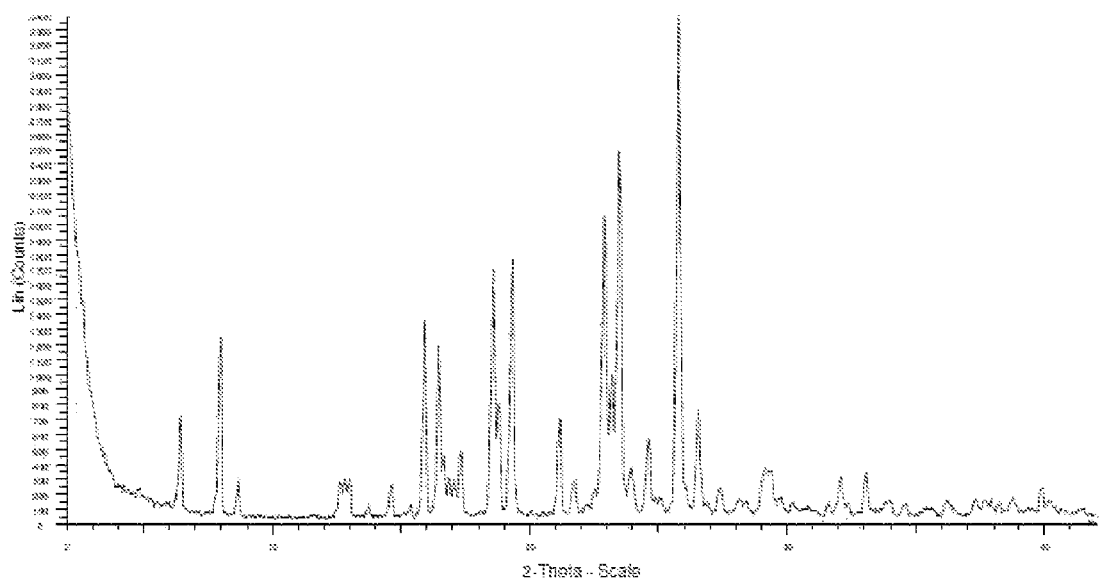
FIG. 21 shows the high resolution XRPD of the fumarate pattern 2 polymorph of Compound I.

A high resolution XRPD of the fumarate pattern 2 polymorph of Compound I is provided in FIG. 21.

Figure 22:
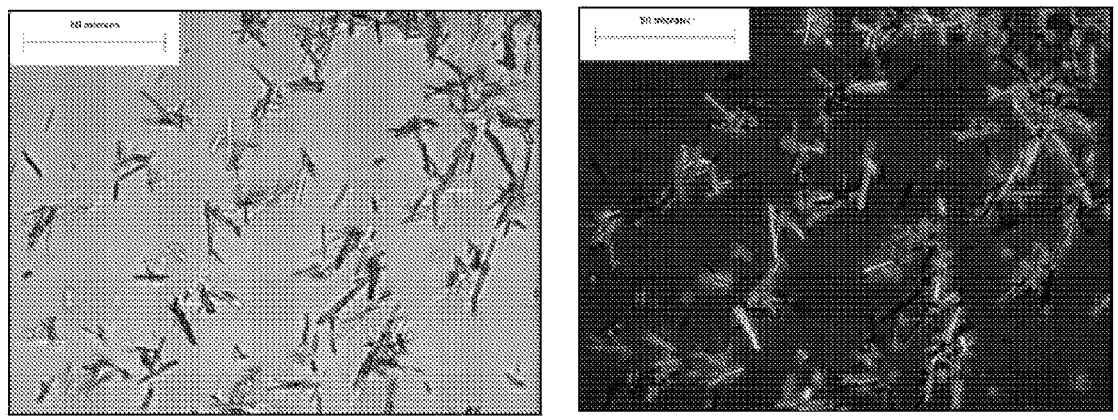
FIG. 22 shows an optical microscopy photograph of the fumarate pattern 2 polymorph of Compound I.

An optical microscopy photograph of the fumarate pattern 2 polymorph of Compound I is provided in FIG. 22.

Figure 23:
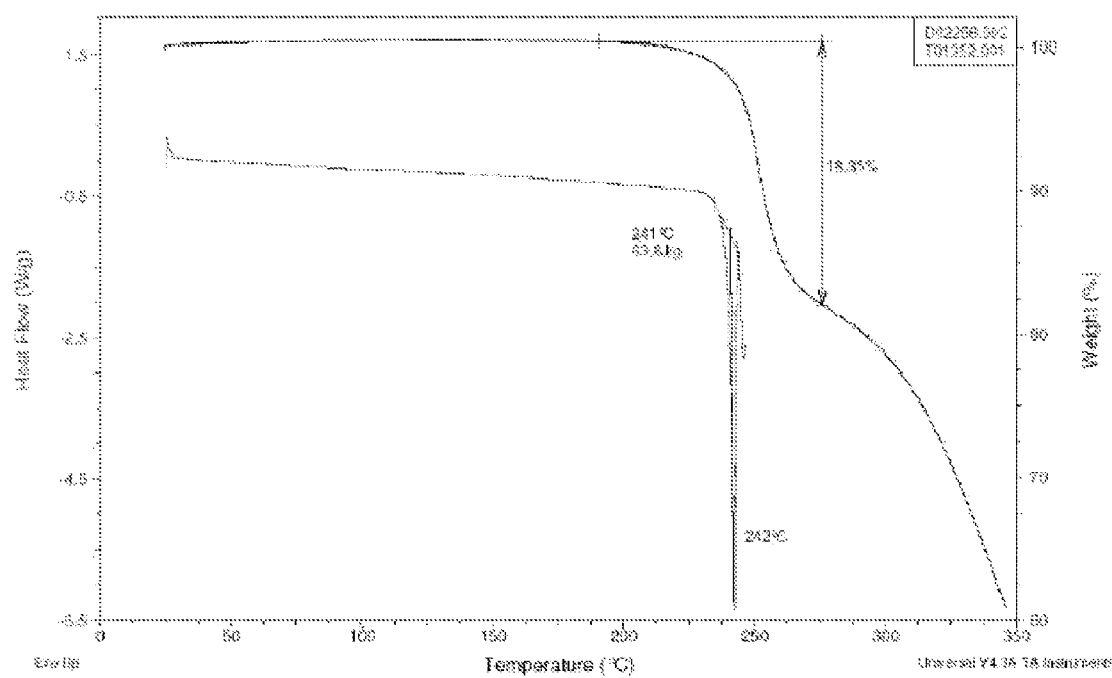
FIG. 23 shows a recording of the TGA/DSC at 10° C./min of the fumarate pattern 2 polymorph of Compound I, wherein the upper trace represents the percent weight as a function of temperature and the lower trace represents the heat flow as a function of temperature.

The recording of the TGA/DSC at 10° C./min of the fumarate pattern 2 polymorph of Compound I is provided in FIG. 23.

Figure 24:
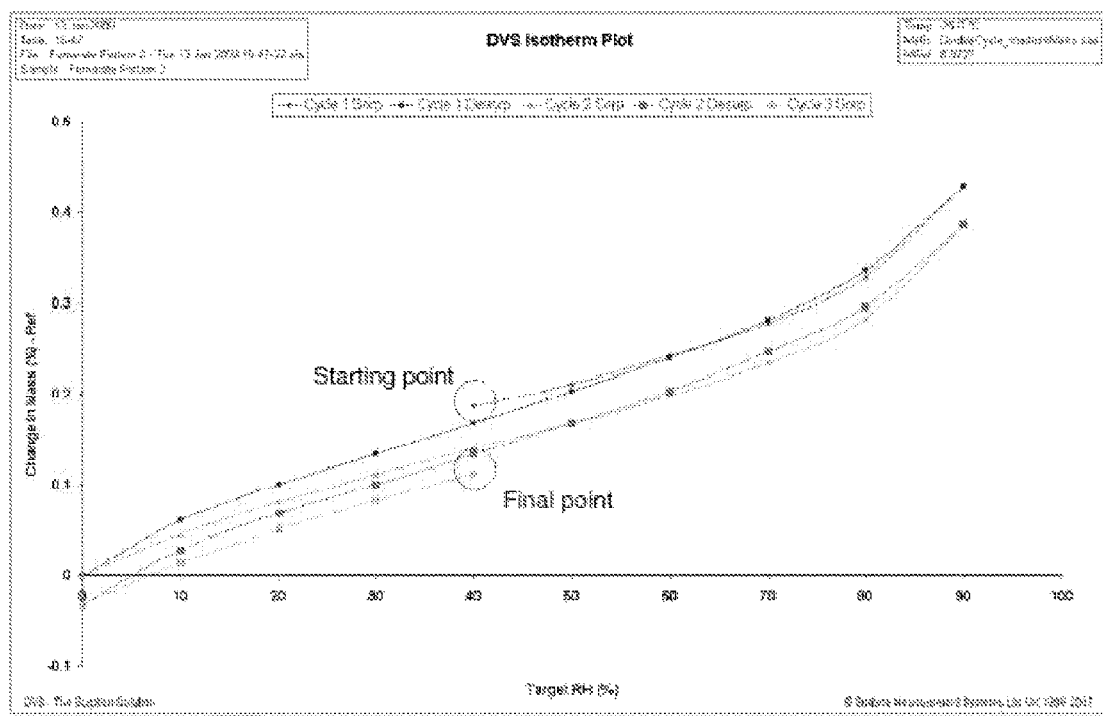
FIGS. 24 and 25 show the GVS at 25° C. curves of the fumarate pattern 2 polymorph of Compound I wherein FIG.
Figure 25:
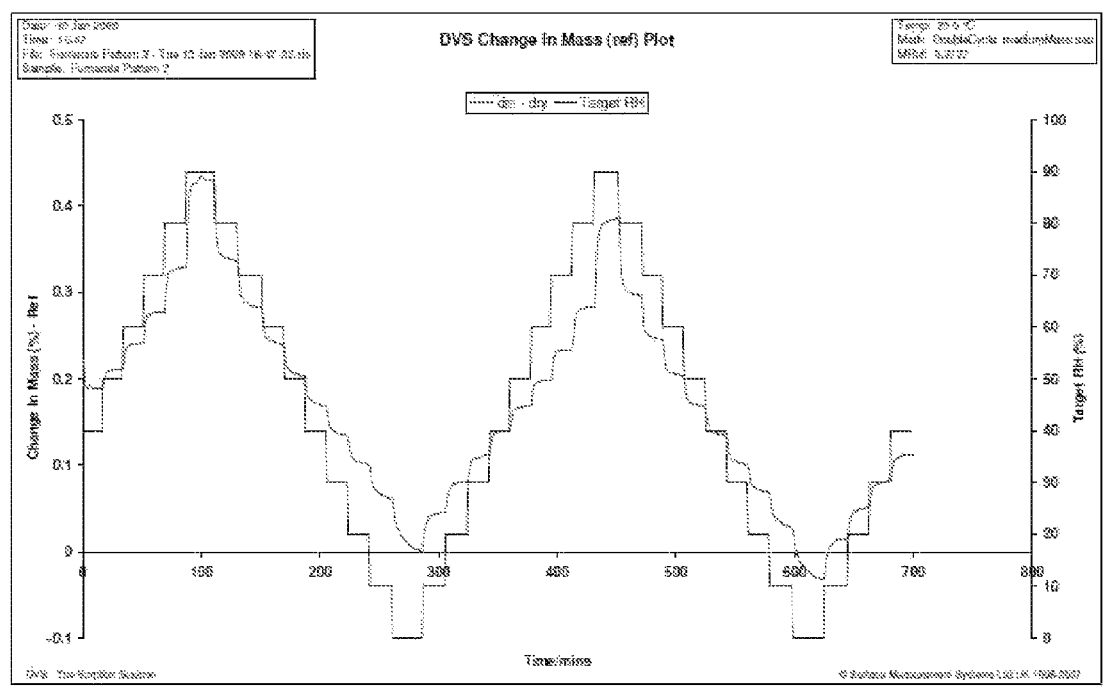

The GVS at 25° C. curves of the fumarate pattern 2 polymorph of Compound I are provided in FIGS. 24 and 25.

A XRPD of the fumarate pattern 2 polymorph of Compound I after GVS study is illustrated in FIG. 18.

Table 9 is a summary of the characterisation of the fumarate pattern 2 polymorph of Compound I.

TABLE 9

Summary of Characterisation Fumiarate Pattern 2 of Compound 1

| Experiment | Comments |
|---|---|
| $^1$H NMR (400 MHz, DMSO, d6) | The $^1$H NMR spectrum was consistent with the mono-fumarate salt. |
| HPLC purity | 97.5% area-3 main impurities were measured at 1.74; 0.33 and 0.10% area. |
| XRPD stability (40° C./75% R.H.) | XPRD of fumarate pattern 2 showed good crystallinity, and no change was observed after 2 weeks of storage at 40° C./75% R.H. |
| Optical Microscopy | The material displays birefringence under polarised light; the particles have needle-like morphology. |
| TGA/DSC @ 10° C./min | No mass loss recorded in TGA until the salt dissociation at circa. 250° C. The melt was recorded at 240° C. (onset) in DSC. |
| GVS @ 25° C. | No hydration phenomenon was observed and the isotherms showed less than 0.5 wt % difference between 0 and 90% relative humidity. No changes in the XRPD pattern (fumarate pattern 2) were detected after the experiment. |
| Ion Chromatography | 0.95 eq. of fumaric acid |
| Thermodynamic stability in water | 0.029 mg/mL, final pH = 3.80 |

Example 6

Preparation and Characterization of the Besylate Salt of 14-methyl-20-Oxa-5,7,14,27-tetraazatetracyclo-[19.3.1.12,6.18,12]heptacosa-1(25),2,4,6,8,10,12 (26),16,21,23-decaene (Compound I)

The free base of Compound I (100 mg, 0.268 mmol) was dissolved at 50° C. in 15 volumes of THF. After homogenisation, the solution was treated with 1 eq. of benzenesulfonic acid (0.268 mL of a 1 M solution in THF). The reaction mixture was then subjected to maturation cycles from room temperature to 50° C. (8 hour cycles) for a 12 hour period. The resulting solid was filtered under vacuum and dried at room temperature to provide 53 mg of product. XPRD analysis indicates the product is a mixture of besylate pattern 1 and form 1 of the free base of Compound I.

Changing the solvent to MEK and using 2 equivalents of benzenesulfonic acid followed by maturing the reaction mixture at room temperature also afforded the product as a mixture of besylate pattern 1 and form 1 of the free base of Compound I.

Changing the solvent to MEK and using 1 equivalents of benzenesulfonic acid followed by maturation cycles from room temperature to 50° C. (8 hour cycles) for a 12 hour period and obtaining a sample product by hot filtration at 50° C. afforded a product as besylate pattern 1. Upon cooling to room temperature, filtration and drying, the product was obtained as a mixture of besylate pattern 1 and form 1 of the free base of Compound I.

Figure 27:
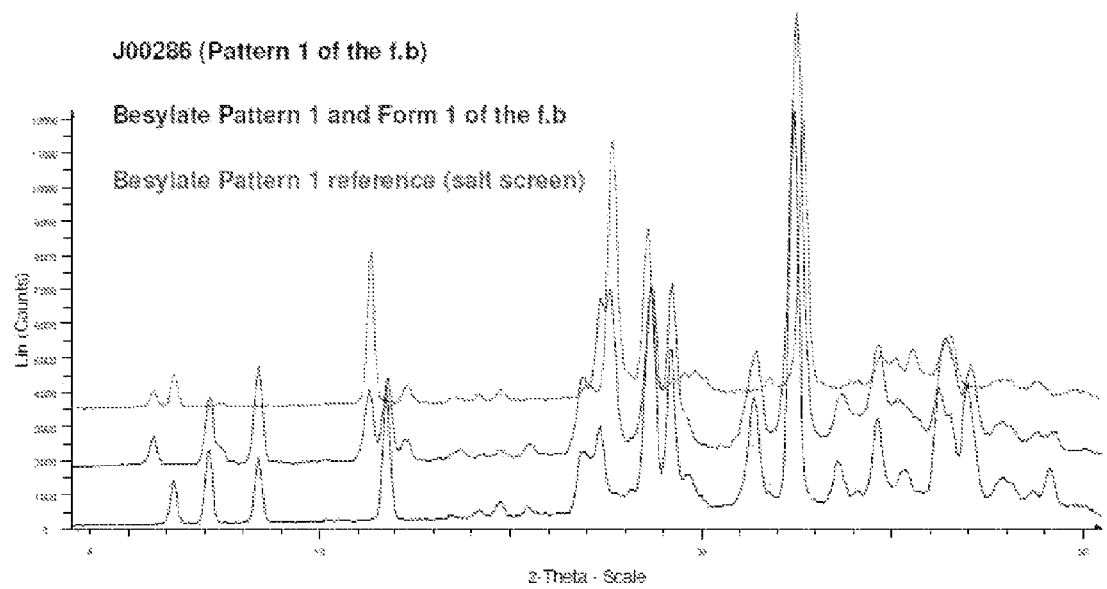
FIG. 27 shows the XRPD of besylate pattern 1 polymorph of Compound I and form 1 of the free base, wherein the upper trace is besylate pattern 1 reference, the middle trace is besylate pattern 1 and form 1 of the free base, and the lower trace is J00286 (pattern 1 of the free base)

A XRPD of the besylate pattern 1 polymorph of Compound I and form 1 of the free base is illustrated in FIG. 27.

Figure 28:
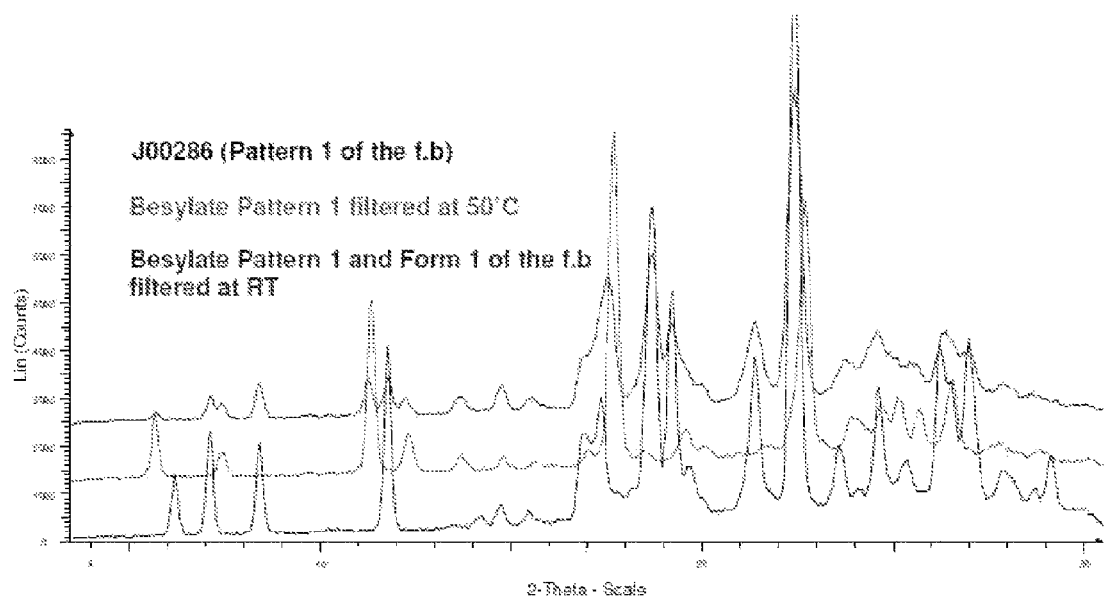
FIG. 28 shows the XRPD of the besylate pattern 1 polymorph of Compound I obtained by hot filtration and the mixture of the besylate pattern 1 polymorph of Compound I and form 1 of the free base obtained by room temperature filtration, wherein the upper trace is besylate pattern 1 and form 1 of the free base filtered at room temperature, the middle trace is besylate pattern 1 filtered at 50° C., and the lower trace is J00286 (pattern 1 of the free base)

A XRPD of the besylate pattern 1 polymorph of Compound I obtained by hot filtration and the mixture of the besylate pattern 1 polymorph of Compound I and form 1 of the free base obtained by room temperature filtration is illustrated in FIG. 28.

Example 7

Polymorph Screen on the Fumarate and Citrate Salts of 14-methyl-20-oxa-5,7,14,27-tetraazatetracyclo-[19.3.1.12,6.18,12]heptacosa-1(25),2,4,6,8,10,12 (26),16,21,23-decaene (Compound I)

An initial polymorphism screen was performed for the fumarate and citrate salts using 10 common class II and III organic solvents (with and without addition of water), plus pure water. 20-25 mg of salt (Fumarate Pattern 2 or Citrate Pattern 1) was weighed into a 2 cm$^3$ vial and 20 volumes of the appropriate solvent was added. The samples were subjected to a series of heat/cool cycles (room temp –50° C., 8 hour cycles). After 3 days, the samples were filtered and the solids were characterised by XRPD analysis. The results for Fumarate Pattern 2 are presented in Table 10 and results for Citrate Pattern 1 are presented in Table 11.

TABLE 10

Polymorph Screen for Fumarate Pattern 2

| | XPRD Characterisation | |
|---|---|---|
| Solvent | w/o water | w/ water (5% v/v) |
| DCM | Fumarate Pattern 2 | Fumarate Pattern 2 |
| Toluene | Fumarate Pattern 2 | Fumarate Pattern 1 |
| Ethyl acetate | Fumarate Pattern 2 | Fumarate Pattern 1 |
| IPA | Fumarate Pattern 2 | Fumarate Pattern 2 |
| THF | Fumarate Pattern 2 | Fumarate Pattern 2 |
| Acetone | Fumarate Pattern 2 | Fumarate Pattern 2 |
| EtOH | Fumarate Pattern 2 | Fumarate Pattern 2 |
| Acetonitrile | Fumarate Pattern 2 | Fumarate Pattern 2 |
| TBME | Fumarate Pattern 2 | Fumarate Pattern 1 |
| nitromethane | Fumarate Pattern 2 | Fumarate Pattern 2 |
| water | Fumarate Pattern 1 | n/a |

TABLE 11

Polymorph Screen for Citrate Pattern 1

| | XPRD Characterisation | |
|---|---|---|
| Solvent | w/o water | w/ water (5% v/v) |
| DCM | Citrate Pattern 1 | Citrate Pattern 3 |
| Toluene | Citrate Pattern 1 | Citrate Pattern 2 |
| Ethyl acetate | Citrate Pattern 1 | Citrate Pattern 2 |
| IPA | Citrate Pattern 1 | Citrate Pattern 1 |

TABLE 11-continued

Polymorph Screen for Citrate Pattern 1

| | XPRD Characterisation | |
|---|---|---|
| Solvent | w/o water | w/ water (5% v/v) |
| THF | Citrate Pattern 1 | Citrate Pattern 2 |
| Acetone | Citrate Pattern 1 | Citrate Pattern 1 |
| EtOH | Citrate Pattern 1 | Citrate Pattern 1 |
| Acetonitrile | Citrate Pattern 1 | Citrate Pattern 2 |
| TBME | Citrate Pattern 1 | Citrate Pattern 2 |
| nitromethane | Citrate Pattern 1 | Citrate Pattern 2 |
| water | Citrate Pattern 2 | n/a |

No transformation of Fumarate Pattern 2 and Citrate Pattern 1 was observed after 3 days of maturation in dried solvents.

Figure 29:
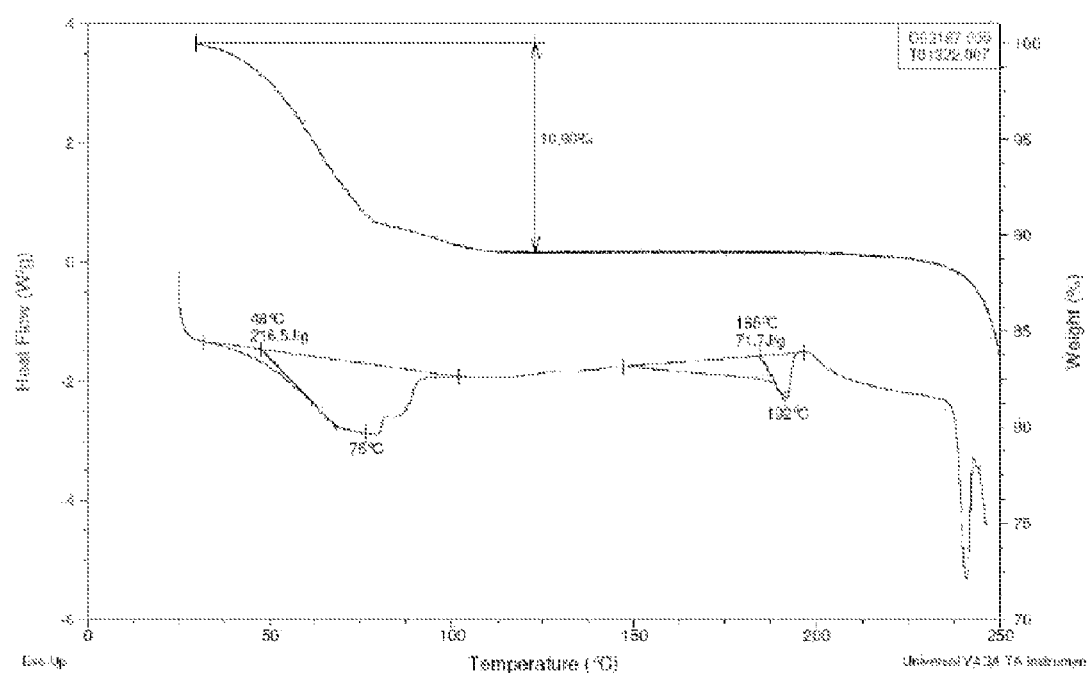
FIG. 29 shows a recording of the TGA/DSC at 10° C./min of the fumarate pattern 1 polymorph of Compound I, wherein the upper trace represents the percent weight as a function of temperature and the lower trace represents the heat flow as a function of temperature.
Figure 30:
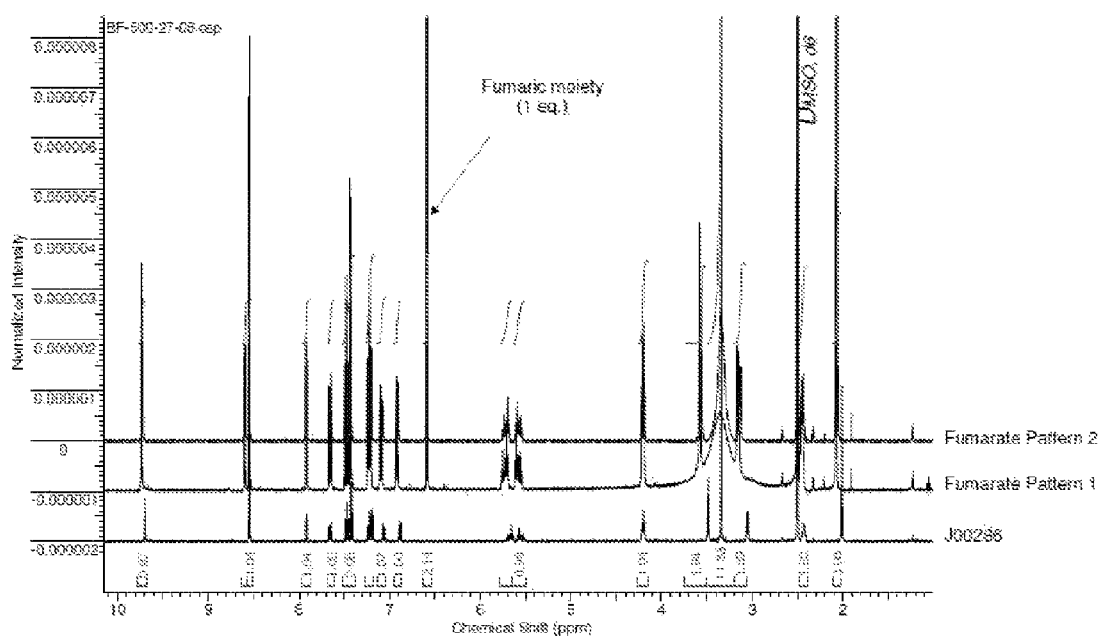
FIG. 30 shows the $^1$H NMR spectrum of the fumarate pattern 1 polymorph of Compound I.
Figure 31:
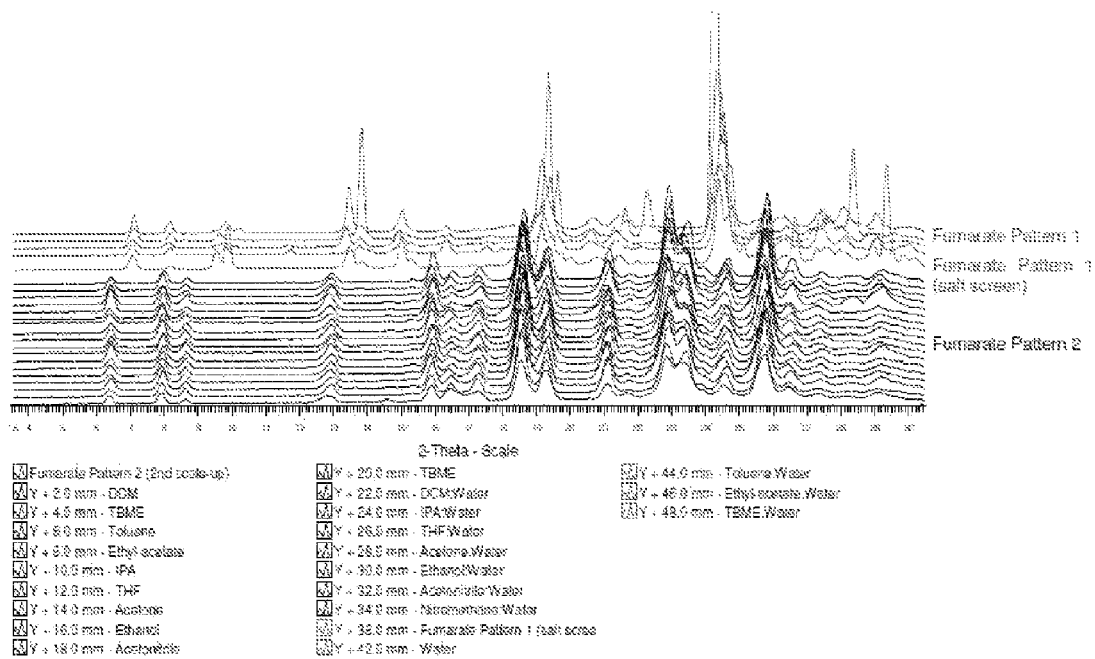
FIG. 31 shows the XRPD data collected during the polymorph screen of the fumarate salt.

Fumarate Pattern 2 transformed to Fumarate Pattern 1 after 3 days of maturation in water, toluene:water, ethyl-acetate:water, and TBME:water. Fumarate Pattern 1 was previously detected, during the salt screen from salt formation in a water:ethanol mixture. This salt was partially characterised by TGA-DSC (see FIG. 29) and $^1$H NMR (see FIG. 30) and could be a hydrated monofumarate salt. The mass loss of 10.9% w/w observed in TGA, might correspond to 3.3 moles of water for a mono-fumarate salt. FIG. 31 shows the XRPD data collected during the polymorph screen of the fumarate salt.

Figure 32:
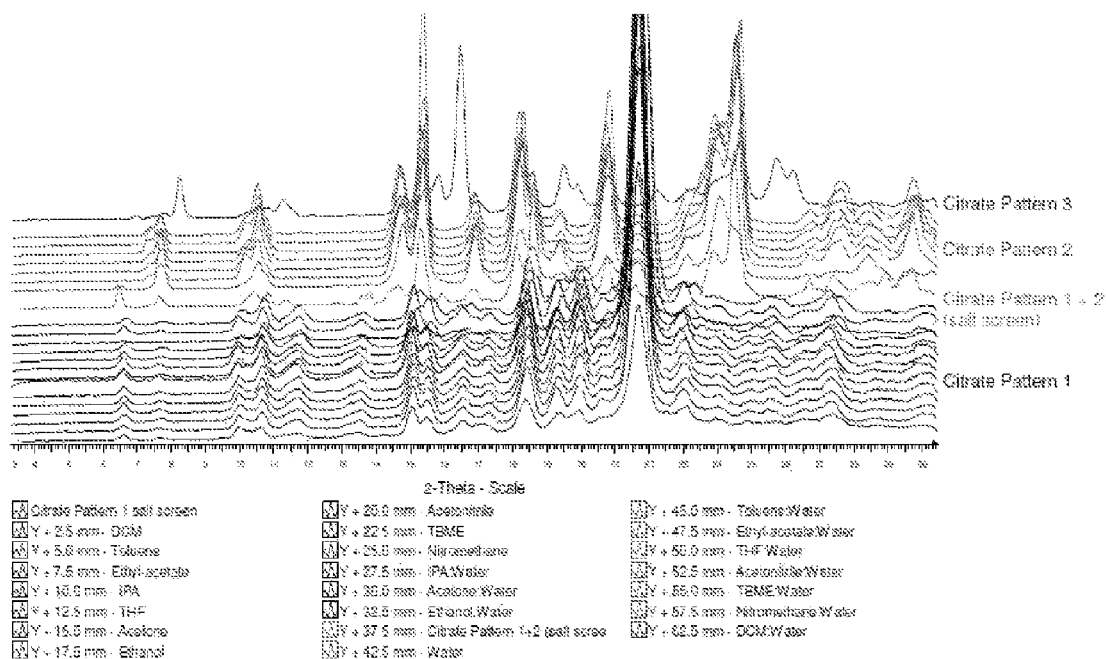
FIG. 32 shows the XRPD data collected during the polymorph screen of the citrate salt.

Citrate Pattern 1 transformed to Citrate Pattern 2 after 3 days of maturation in water, toluene:water, ethyl-acetate:water, THF:water, acetonitrile:water, TBME:water and nitromethane:water. Citrate Pattern 2 was also previously detected as a mixture with Form 1 of the free base, during the main salt screen from a water:ethanol mixture. Furthermore, Citrate Pattern 1 transformed to a new solid phase (Citrate Pattern 3) after slurrying in DCM:water (95:5 v/v). FIG. 32 shows the XRPD data collected during the polymorph screen of the citrate salt.

Procedure for the Synthesis of Fumarate Pattern 1 on Preparative Scale

Figure 33:
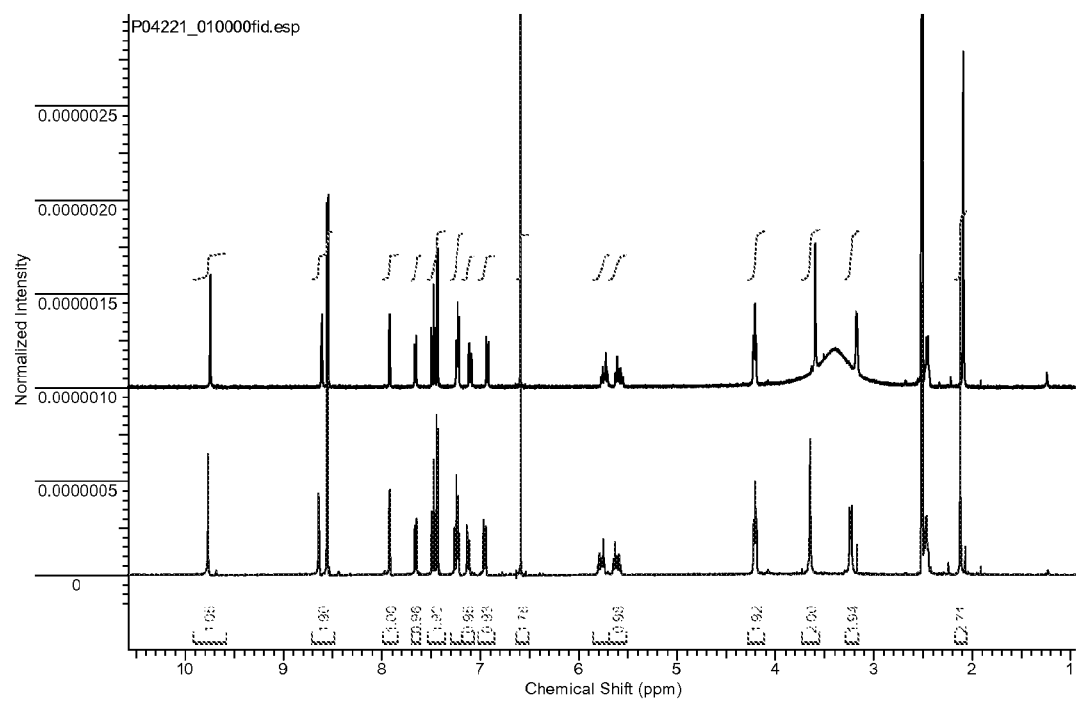
FIG. 33 shows a $^1$H NMR spectrum of the fumarate pattern 1 polymorph of Compound I obtained on a preparative scale.
Figure 34:
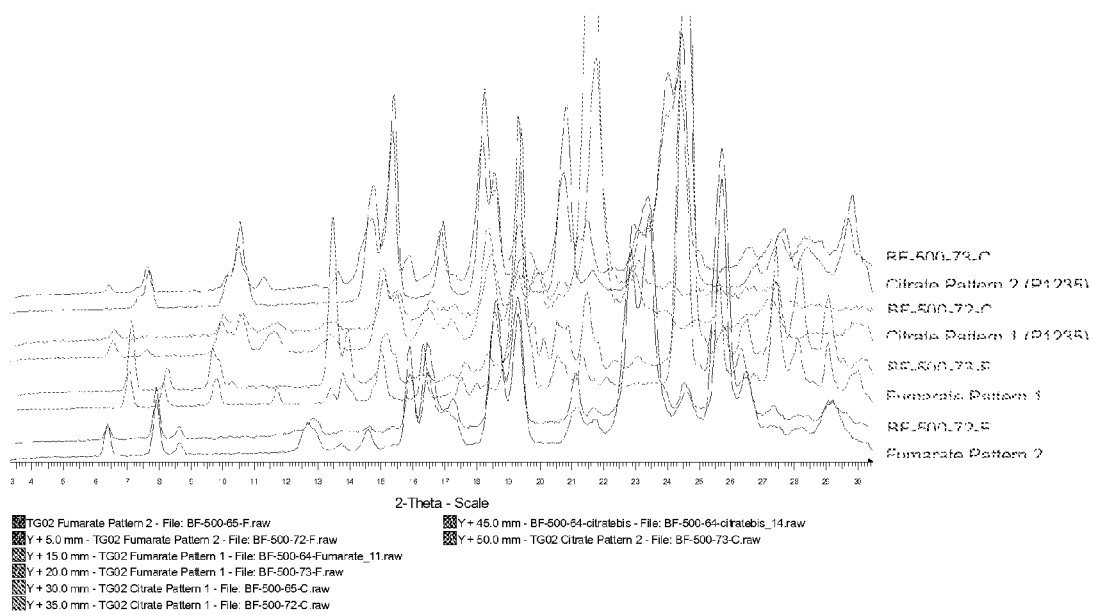
FIG. 34 shows the XRPD of fumarate pattern 1 polymorph of Compound I.
Figure 35:
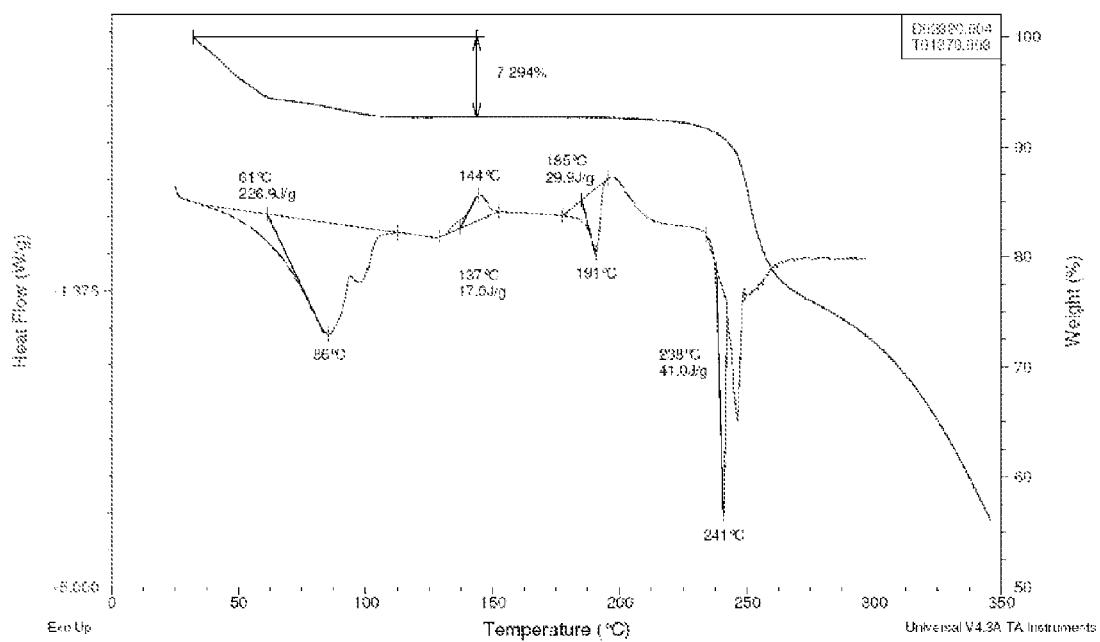
FIG. 35 shows a recording of the TGA/DSC at 10° C./min of the fumarate pattern 1 polymorph of Compound I, wherein the upper trace represents the percent weight as a function of temperature and the lower trace represents the heat flow as a function of temperature.
Figure 36:
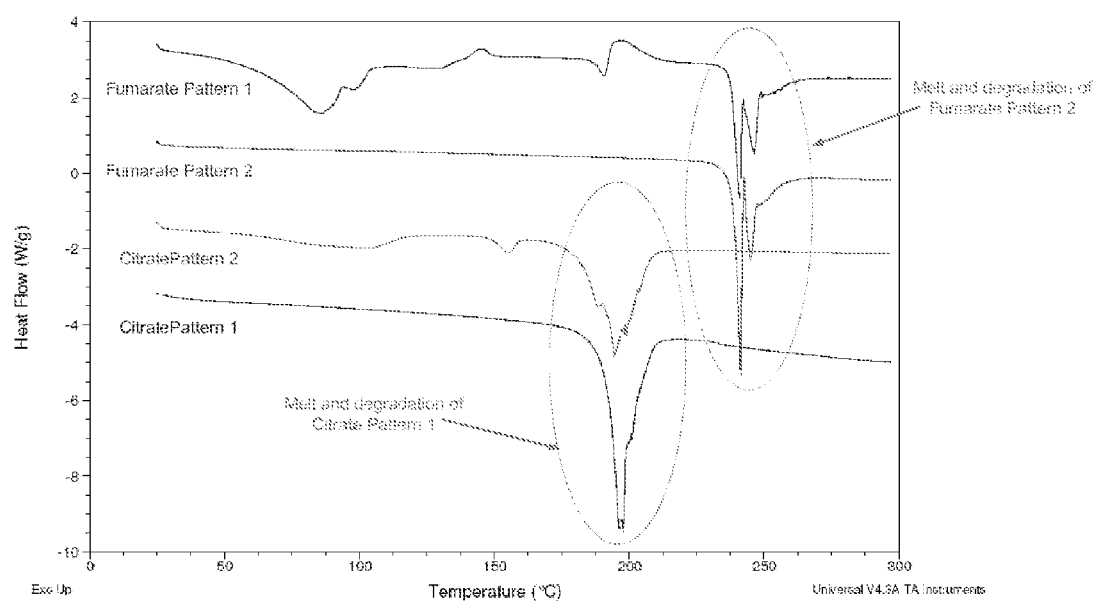
FIG. 36 shows a comparison of the TGA/DSC at 10° C./min of the fumarate pattern 1 and fumarate pattern 2 polymorph of Compound I, and of the citrate pattern 1 and citrate pattern 2 polymorph of Compound I.

The free base of Compound I (200 mg) was dissolved in 50:50 v/v water:ethanol (10 mL) at 60° C. with stirring in a 25 mL conical flask. After complete dissolution, fumaric acid (1.128 mL of a 0.5 M solution in 50:50 (v/v) methanol:THF) was added dropwise to the warm solution and the reaction mixture was maturated in a maturation chamber from room temperature to 50° C. (8 hour cycles) with shaking for 12 hours. The reaction mixture was filtered under vacuum and dried for 12 hours at room temperature to give a yellow solid. The $^1$H NMR is presented in FIG. 33. The XRPD is presented in FIG. 34. The DSC/TGA is presented in FIG. 35. A comparison of the TGA/DSC curves for Fumarate Pattern 1 and 2 is provided in FIG. 36.

Procedure for the Synthesis of Citrate Pattern 2 on Preparative Scale

Figure 37:
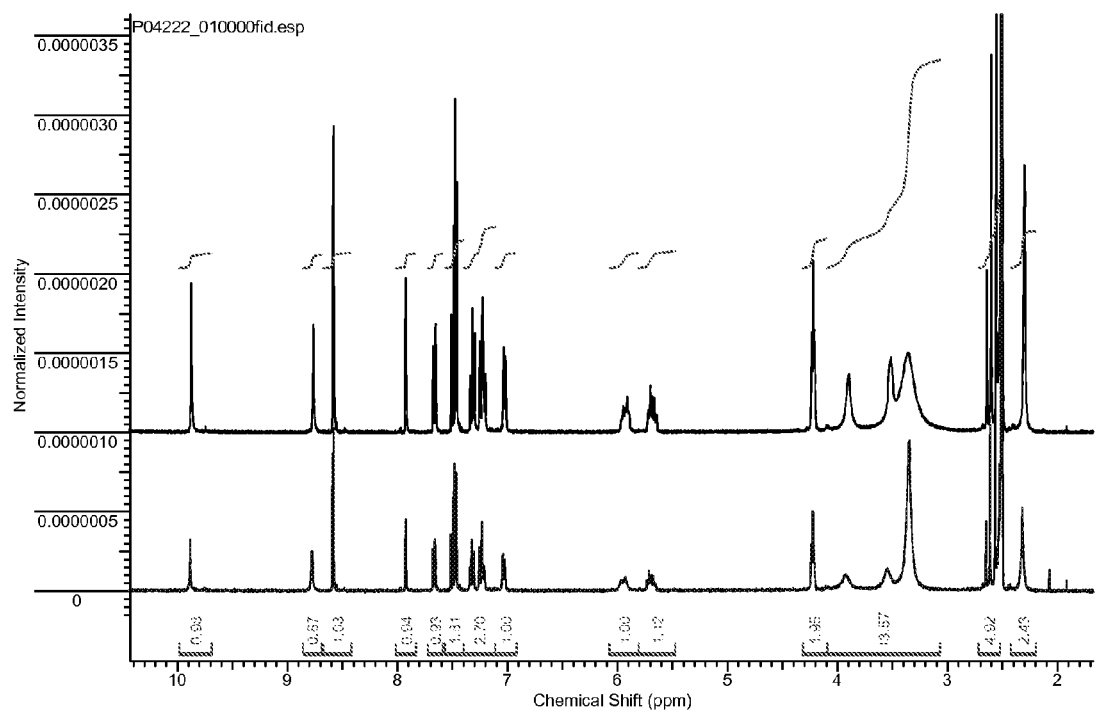
FIG. 37 shows a $^1$H NMR spectrum of the citrate pattern 2 polymorph of Compound I obtained on a preparative scale.
Figure 38:
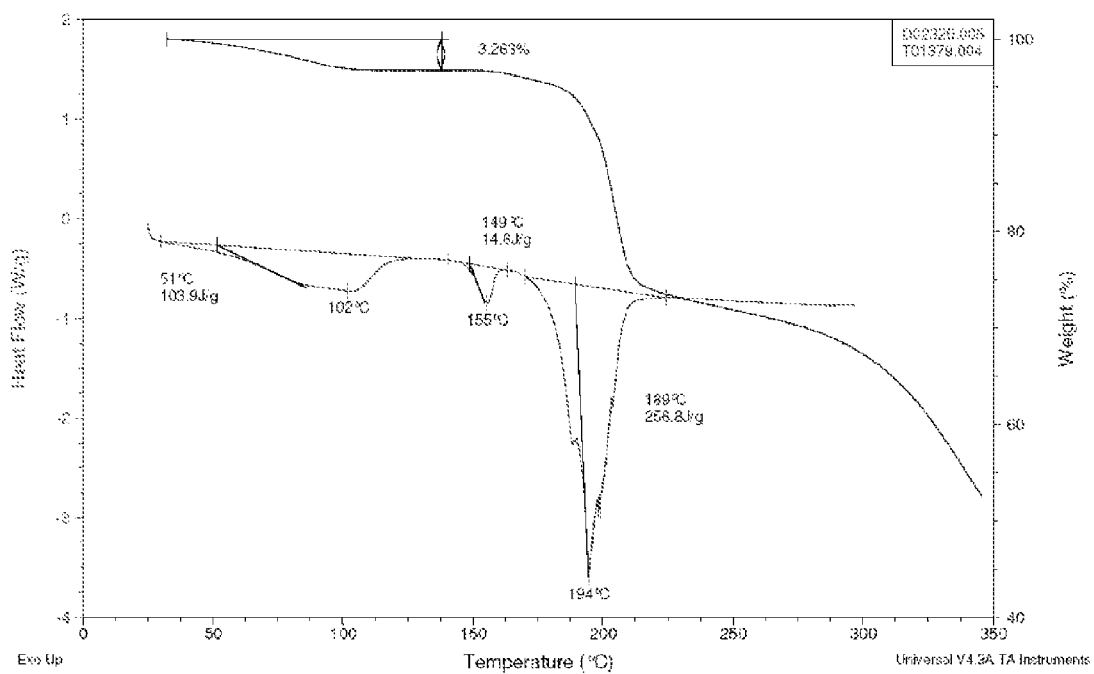
FIG. 38 shows a recording of the TGA/DSC at 10° C./min of the citrate pattern 2 polymorph of Compound I, wherein the upper trace represents the percent weight as a function of temperature and the lower trace represents the heat flow as a function of temperature.

The free base of Compound I (200 mg) was dissolved in 50:50 v/v water:ethanol (10 mL) at 60° C. with stirring in a 25 mL conical flask. After complete dissolution, a seed crystal of Citrate Pattern 2 was added followed by citric acid (0.564 mL of a 1.0 M solution in THF) added dropwise to the warm solution and the reaction mixture was maturated in a maturation chamber from room temperature to 50° C. (8 hour cycles) with shaking for 12 hours. The reaction mixture was filtered under vacuum and dried for 12 hours at room temperature to give a yellowish solid. The $^1$H NMR is presented in FIG. 37. The XRPD is presented in FIG. 34. The DSC/TGA is presented in FIG. 38. A comparison of the TGA/DSC curves for Citrate Pattern 1 and 2 is provided in FIG. 36.

Example 8

Stability Study of the Fumarate and Citrate Salts of 14-methyl-20-oxa-5,7,14,27-tetraazatetracyclo-[19.3.1.12,6.18,12]heptacosa-1(25),2,4,6,8,10,12 (26),16,21,23-decaene (Compound I)

Purpose:

To compare the rate of hydration of fumarate pattern 2 against citrate pattern 1. Test medium was prepared by dissolving methocel (4 g) in water (196 mL) to afford a 2% (w/w) solution. After stirring for 12 hours to ensure a homogenous solution is obtained, Tween 80 (800 mg) and water (600 mL) was added and the mixture stirred for an additional 12 hours to homogenise.

For the 1 mg/mL concentration experiments, the anhydrous polymorph (30 mg of either citrate pattern 1 or fumarate pattern 2) was placed into a 40 mL glass tube. Test medium (30 mL) was added and each sample was maturated at the indicated temperature and condition (−20° C., 4° C., room temperature with stirring and room temperature without stirring). A parallel series of samples was prepared with the addition of a hydrated polymorph seed crystal (either citrate pattern 2 or fumarate pattern 1). The samples were monitored over time by XRPD to determine the rate of hydration of the anhydrous polymorph.

For the 10 mg/mL concentration experiments, the anhydrous polymorph (50 mg of either citrate pattern 1 or fumarate pattern 2) was placed into a 20 mL glass tube. Test medium (5 mL) was added and each sample was maturated at the indicated temperature and condition (−20° C., 4° C., room temperature with stirring and room temperature without stirring). A parallel series of samples was prepared with the addition of a hydrated polymorph seed crystal (either citrate pattern 2 or fumarate pattern 1). The samples were monitored over time by XRPD to determine the rate of hydration of the anhydrous polymorph.

The results from the stability study are presented in Table 12 and indicate the kinetics of hydration of the citrate salt are slower than for the fumarate salt. Seeding and stirring are two parameters which increase the kinetics of transformation with seeding reducing the nucleation time and stirring accelerating the permanent dissolution-recrystallisation phenomenon.

TABLE 12

Time points (hours) where transformation was observed

| | | | −20° C. | 4° C. | 20-25° C. (without stirring) | 20-25° C. (under stirring) |
|---|---|---|---|---|---|---|
| TG02 Fumarate salt | P2 | 1 mg/mL | 120 | 120 | 48 | 24 |
| | | 10 mg/mL | No conversion | No conversion | 120 | 48 |

TABLE 12-continued

| | | | Time points (hours) where transformation was observed | | | |
|---|---|---|---|---|---|---|
| | | | −20° C. | 4° C. | 20-25° C. (without stirring) | 20-25° C. (under stirring) |
| | P2 + seeds of P1 | 1 mg/mL | 24 | 6 | 48 | 24 |
| | | 10 mg/mL | No conversion | 24 | 24 | 24 |
| TG02 Citrate salt | P1 | 1 mg/mL | No conversion | No conversion | Clear Solution | 120 |
| | | 10 mg/mL | No conversion | No conversion | No conversion | 48 |
| | P1 + seeds of P2 | 1 mg/mL | No conversion | 120 | 120 | 24 |
| | | 10 mg/mL | No conversion | No conversion | No conversion | 120 |

Example 9

Formulation of 14-methyl-20-oxa-5,7,14,27-tetraaza-tetracyclo-[19.3.1.12,6.18,12]heptacosa-1(25),2,4,6,8,10,12(26),16,21,23-decaene citrate form 1

A pharmaceutical composition comprising 100 mg of active ingredient per capsule is prepared according to the formula and process described below.

The ingredients are dry blended to homogenity and the bulk composition dispensed into the hard gelatin capsule shells using a Minicap 100 semi-automatic capsule filler.

| Ingredient | % w/w | mg/capsule | g/batch |
|---|---|---|---|
| 14-methyl-20-oxa-5,7,14,27-tetraazatetracyclo-[19.3.1.12,6.18,12]heptacosa-1(25),2,4,6,8,10,12(26),16,21,23-decaene citrate form 1 | 40.00 | 100.00 | 2320.00 |
| Lactose Monohydrate, NF (316 Fast Flo) | 49.25 | 123.13 | 2856.50 |
| Croscarmellose Sodium, NF (AcDiSol) | 10.00 | 25.00 | 580.00 |
| Magnesium Stearate, NF (vegetable grade MF-2-V) | 0.75 | 1.88 | 43.50 |
| TOTAL | 100.00 | 250.00 | 5800.00 |
| Size 1 Hard Gelatin capsule Shells | | 23,200 capsules | |

What is claimed is:

1. A crystalline citrate salt of 14-methyl-20-oxa-5,7,14,27-tetraazatetracyclo-[19.3.1.12,6.18,12]heptacosa-1(25),2,4,6,8,10,12(26),16,21,23-decaene exhibiting the x-ray powder diffraction pattern of FIG. 13.

2. The crystalline citrate salt of claim 1 having a melting point of 191° C. as determined by differential scanning calorimetry.

3. A crystalline citrate salt of 14-methyl-20-oxa-5,7,14,27-tetraazatetracyclo-[19.3.1.12,6.18,12]heptacosa-1(25),2,4,6,8,10,12(26),16,21,23-decaene exhibiting a powder x-ray diffraction pattern reflection at 2 theta=21.5°.

4. The crystalline citrate salt of claim 3 further characterized by a powder x-ray diffraction pattern reflection at 2 theta-15.0°.

5. The crystalline citrate salt of claim 3 or 4 further characterized by a powder x-ray diffraction pattern reflection at 2 theta=19.8°.

6. The crystalline citrate salt of claim 3, 4, or 5 further characterized by a melting point of 191° C. as determined by differential scanning calorimetry.

7. A pharmaceutical composition comprising a therapeutically effective amount of the crystalline citrate salt of 14-methyl-20-oxa-5,7,14,27-tetraazatetracyclo-[19.3.1.12,6.18,12] heptacosa-1(25),2,4,6,8,10,12(26),16,21,23-decaene exhibiting the x-ray powder diffraction pattern of FIG. 13.

8. A pharmaceutical composition comprising a therapeutically effective amount of the crystalline citrate salt of 14-methyl-20-oxa-5,7,14,27-tetraazatetracyclo-[19.3.1.12,6.18,12] heptacosa-1(25),2,4,6,8,10,12(26),16,21,23-decaene exhibiting the x-ray powder diffraction pattern of FIG. 13, wherein the pharmaceutical composition is substantially free of any other crystalline citrate salt.

9. A pharmaceutical composition comprising a therapeutically effective amount of the crystalline citrate salt of 14-methyl-20-oxa-5,7,14,27-tetraazatetracyclo-[19.3.1.12,6.18,12] heptacosa-1(25),2,4,6,8,10,12(26),16,21,23-decaene exhibiting a powder x-ray diffraction pattern reflection at 2 theta=21.5°.

10. The pharmaceutical composition of claim 9, wherein the crystalline citrate salt of 14-methyl-20-oxa-5,7,14,27-tetraazatetracyclo-[19.3.1.12,6.18,12] heptacosa-1(25),2,4,6,8,10,12(26),16,21,23-decaene is further characterized by a powder x-ray diffraction pattern reflection at 2 theta=15.0°.

11. The pharmaceutical composition of claim 9 or 10, wherein the crystalline citrate salt of 14-methyl -20-oxa-5,7,14,27-tetraazatetracyclo-[19.3.1.12,6.18,12] heptacosa-1(25),2,4,6,8,10,12(26),16,21,23-decaene is further characterized by a powder x-ray diffraction pattern reflection at 2 theta=19.8°.

12. The pharmaceutical composition of claim 9, 10, or 11, wherein the crystalline citrate salt of 14-methyl-20-oxa-5,7,14,27-tetraazatetracyclo-[19.3.1.12,6.18,12] heptacosa-1(25),2,4,6,8,10,12(26),16,21,23-decaene is further characterized by a melting point of 191° C. as determined by differential scanning calorimetry.

13. A pharmaceutical composition comprising a therapeutically effective amount of the crystalline citrate salt of 14-methyl-20-oxa-5,7,14,27-tetraazatetracyclo-[19.3.1.12, 6.18,12] heptacosa-1(25),2,4,6,8,10,12(26),16,21,23-decaene exhibiting a powder x-ray diffraction pattern reflection at 2 theta=21.5°, wherein the pharmaceutical composition is substantially free of any other crystalline citrate salt.

14. The pharmaceutical composition of claim 13, wherein the crystalline citrate salt of 14-methyl-20-oxa-5,7,14,27-tetraazatetracyclo-[19.3.1.12,6.18,12] heptacosa-1(25),2,4,6,8,10,12(26),16,21,23-decaene exhibiting a powder x-ray diffraction pattern reflection at 2 theta=21.5° is further characterized by a reflection at 2 theta=15.0°.

15. The pharmaceutical composition of claim 13 or 14, wherein the crystalline citrate salt of 14-methyl-20-oxa-5,7, 14,27-tetraazatetracyclo-[19.3.1.1.2,6.1.8,12] heptacosa-1(25),2,4,6,8,10,12(26),16,21,23-decaene exhibiting a powder x-ray diffraction pattern reflection at 2 theta=21.5° is further characterized by a reflection at 2 theta=19.8°.

16. The pharmaceutical composition of claim 13, 14, or 15, wherein the crystalline citrate salt of 14-methyl-20-oxa-5,7,14,27-tetraazatetracyclo-[19.3.1.1.2,6.1.8,12]heptacosa-1(25),2,4,6,8,10,12(26),16,21,23-decaene exhibiting a powder x-ray diffraction pattern reflection at 2 theta=21.5° is further characterized by a melting point of 191° C. as determined by differential scanning calorimetry.

* * * * *